US010272208B2

United States Patent
Watanabe

(10) Patent No.: US 10,272,208 B2
(45) Date of Patent: Apr. 30, 2019

(54) APPARATUS AND SYSTEM FOR CONTROLLING PERMEATION AND DIFFUSION OF SOLUTE AND/OR SOLVENT LOCALLY

(71) Applicant: AceMedic Inc., Okayama (JP)

(72) Inventor: Masami Watanabe, Okayama (JP)

(73) Assignee: AceMedic Inc., Okayama (JP)

( * ) Notice: Subject to any disclaimer, the term of this patent is extended or adjusted under 35 U.S.C. 154(b) by 242 days.

(21) Appl. No.: 14/685,153

(22) Filed: Apr. 13, 2015

(65) Prior Publication Data

US 2016/0256634 A1 Sep. 8, 2016

(30) Foreign Application Priority Data

Apr. 14, 2014 (JP) ................. 2014-083036

(51) Int. Cl.
*A61M 5/32* (2006.01)
*A61M 1/00* (2006.01)
*A61M 25/00* (2006.01)
*A61B 17/34* (2006.01)

(52) U.S. Cl.
CPC ......... *A61M 5/321* (2013.01); *A61B 17/3478* (2013.01); *A61M 1/0086* (2014.02); *A61M 25/007* (2013.01); *A61B 2217/005* (2013.01); *A61M 2202/09* (2013.01); *A61M 2205/3331* (2013.01); *A61M 2250/00* (2013.01)

(58) Field of Classification Search
CPC .. A61M 5/321; A61M 1/0086; A61M 25/007; A61M 2250/00; A61M 2205/3331; A61M 2202/09; A61B 2217/005; A61B 17/3478
See application file for complete search history.

(56) References Cited

U.S. PATENT DOCUMENTS

| 6,753,005 | B1 | 6/2004 | Pietronigro et al. |
| 7,780,638 | B1* | 8/2010 | Deniega ............ A61M 25/0043 604/264 |
| 2001/0025155 | A1* | 9/2001 | Yoon ................ A61B 17/00234 604/1 |
| 2003/0181824 | A1* | 9/2003 | Odland ............... A61M 1/0023 600/573 |

(Continued)

FOREIGN PATENT DOCUMENTS

| JP | 2000-279514 | 10/2000 |
| JP | 2005-535393 | 11/2005 |

(Continued)

OTHER PUBLICATIONS

Barua et al. "Convection-Enhanced Drug Delivery to the Brain: Therapeutic Potential and Neuropathological Considerations," Brain Pathology, 2014, vol. 24, No. 2, pp. 117-127.

(Continued)

*Primary Examiner* — Bhisma Mehta
*Assistant Examiner* — Hamza A Darb
(74) *Attorney, Agent, or Firm* — Sheridan Ross P.C.

(57) ABSTRACT

A permeation apparatus comprises an aspiration tube; an injection tube; and a water-absorbing cover member for covering at least a distal end of the injection tube and a vicinity of the distal end. The aspiration tube is configured to aspirate a fluid flowing from the water-absorbing cover member into the aspiration tube.

14 Claims, 26 Drawing Sheets

(56) References Cited

U.S. PATENT DOCUMENTS

2008/0200877 A1     8/2008    Panotopoulos

FOREIGN PATENT DOCUMENTS

| | | |
|---|---|---|
| JP | 2009-506817 | 2/2009 |
| JP | 2009-508551 | 3/2009 |
| JP | 2012-513839 | 6/2012 |
| WO | WO 2007/031765 | 3/2007 |
| WO | WO 2010/080667 | 7/2010 |
| WO | WO 2013/084945 | 6/2013 |
| WO | WO 2014/014495 | 1/2014 |
| WO | WO 2014/018595 | 1/2014 |
| WO | WO 2014/023551 | 2/2014 |

OTHER PUBLICATIONS

Bobo et al. "Convection-enhanced delivery of macromolecules in the brain," Proceedings of the National Academy of Sciences, USA, Mar. 1994, vol. 91, No. 6, pp. 2076-2080.

Chen et al. "Variables affecting convection-enhanced delivery to the striatum: a systematic examination of rate of infusion, cannula size, infusate concentration, and tissue-cannula sealing time," Journal for Neurosurgery, Feb. 1999, vol. 90, No. 2, pp. 315-320.

Germani et al. "Clinical outcomes of radiofrequency ablation, percutaneous alcohol and acetic acid injection for hepatocelullar carcinoma: A meta-analysis," Journal of Hepatology, 2010, vol. 52, No. 3, pp. 380-388.

King et al. "Comparison of Intraprostatic Ethanol Diffusion Using a Microporous Hollow Fiber Catheter Versus a Standard Needle," The Journal of Urology, May 2012, vol. 187, No. 5, pp. 1898-1902.

Oh et al. "Improved distribution of small molecules and viral vectors in the murine brain using a hollow fiber catheter," Journal of Neurosurgery, Sep. 2007, vol. 107, No. 3, pp. 568-577.

Plante et al. "Phase I/II Examination of Transurethral Ethanol Ablation of the Prostate for the Treatment of Symptomatic Benign Prostatic Hyperplasia," The Journal of Urology, Mar. 2007, vol. 177, No. 3, pp. 1030-1035.

Official Action with English Translation for Japan Patent Application No. 2015-079907, dated Nov. 21, 2017, 11 pages.

Official Action with English Translation for Japan Patent Application No. 2015-079907, dated Mar. 20, 2018, 11 pages.

\* cited by examiner

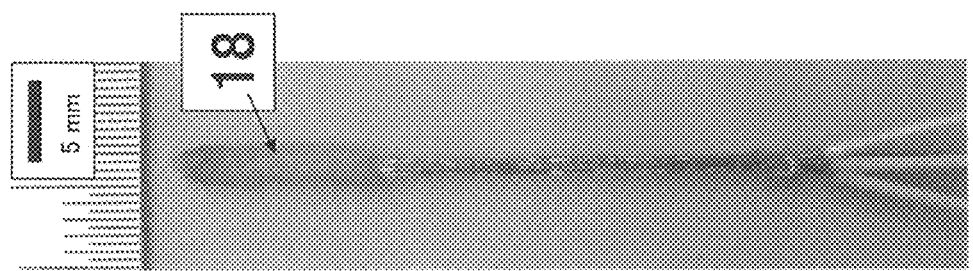
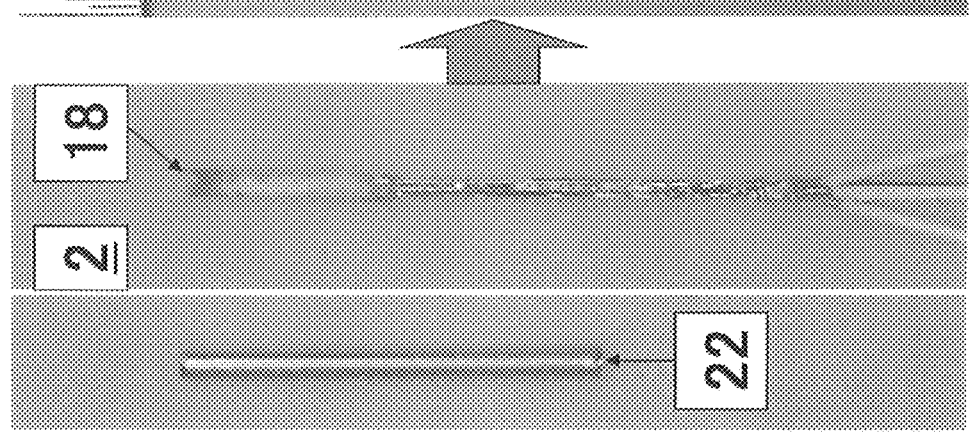
FIG. 3A
FIG. 3B

1: PVA (polyvinyl alcohol) material
2: 80% rayon and 20% polyester material
3: melamine foam material

Fig. 7B

| Scale | Injection amount (μl/min) Capacity of syringe ( Adaptive syringe : Capacity scale 60 mm ) | | | | | | | | | | | Entire operation time | |
|---|---|---|---|---|---|---|---|---|---|---|---|---|---|
| | 10 μl | 25 μl | 50 μl | 100 μl | 250 μl | 500 μl | 1 ml | 1.25 ml | 2.5 ml | 5 ml | 10 ml | Minutes | |
| 1 | 0.001 | 0.0025 | 0.005 | 0.01 | 0.025 | 0.05 | 0.1 | 0.125 | 0.25 | 0.5 | 1.0 | 10000 |
| 2 | 0.002 | 0.005 | 0.01 | 0.02 | 0.05 | 0.1 | 0.2 | 0.25 | 0.5 | 1.0 | 2.0 | 5000 |
| 3 | 0.005 | 0.0125 | 0.025 | 0.05 | 0.125 | 0.25 | 0.5 | 0.625 | 1.25 | 2.5 | 5.0 | 2000 |
| 4 | 0.008 | 0.02 | 0.04 | 0.08 | 0.2 | 0.4 | 0.8 | 1.0 | 2.0 | 4.0 | 8.0 | 1250 |
| 5 | 0.010 | 0.025 | 0.05 | 0.10 | 0.25 | 0.5 | 1.0 | 1.25 | 2.5 | 5.0 | 10 | 1000 |
| 6 | 0.015 | 0.0375 | 0.075 | 0.15 | 0.375 | 0.75 | 1.5 | 1.875 | 3.75 | 7.5 | 15 | 667 |
| 7 | 0.02 | 0.05 | 0.1 | 0.2 | 0.5 | 1.0 | 2.0 | 2.5 | 5.0 | 10 | 20 | 500 |
| 8 | 0.03 | 0.0625 | 0.125 | 0.25 | 0.625 | 1.25 | 2.5 | 3.125 | 6.25 | 12.5 | 25 | 400 |
| 9 | 0.03 | 0.075 | 0.15 | 0.3 | 0.75 | 1.5 | 3.0 | 3.75 | 7.5 | 15 | 30 | 333 |
| 10 | 0.04 | 0.1 | 0.2 | 0.4 | 1.0 | 2.0 | 4.0 | 5.0 | 10 | 20 | 40 | 250 |
| 11 | 0.05 | 0.125 | 0.25 | 0.5 | 1.25 | 2.5 | 5.0 | 6.25 | 12.5 | 25 | 50 | 200 |
| 12 | 0.08 | 0.2 | 0.4 | 0.8 | 2.0 | 4.0 | 8.0 | 10 | 20 | 40 | 80 | 125 |
| 13 | 0.1 | 0.25 | 0.5 | 1.0 | 2.5 | 5.0 | 10 | 12.5 | 25 | 50 | 100 | 100 |
| 14 | 0.2 | 0.5 | 1.0 | 2.0 | 5.0 | 10 | 20 | 25 | 50 | 100 | 200 | 50 |
| 15 | 0.5 | 1.25 | 2.5 | 5.0 | 12.5 | 25 | 50 | 62.5 | 125 | 250 | 500 | 20 |
| 16 | 1.0 | 2.5 | 5.0 | 10 | 25 | 50 | 100 | 125 | 250 | 500 | 1000 | 10 |

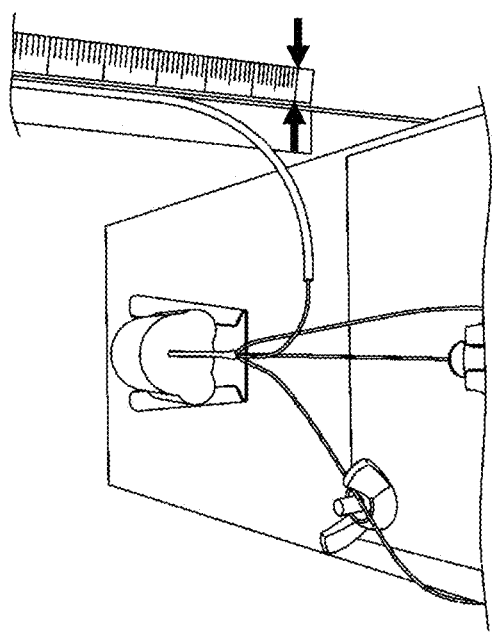

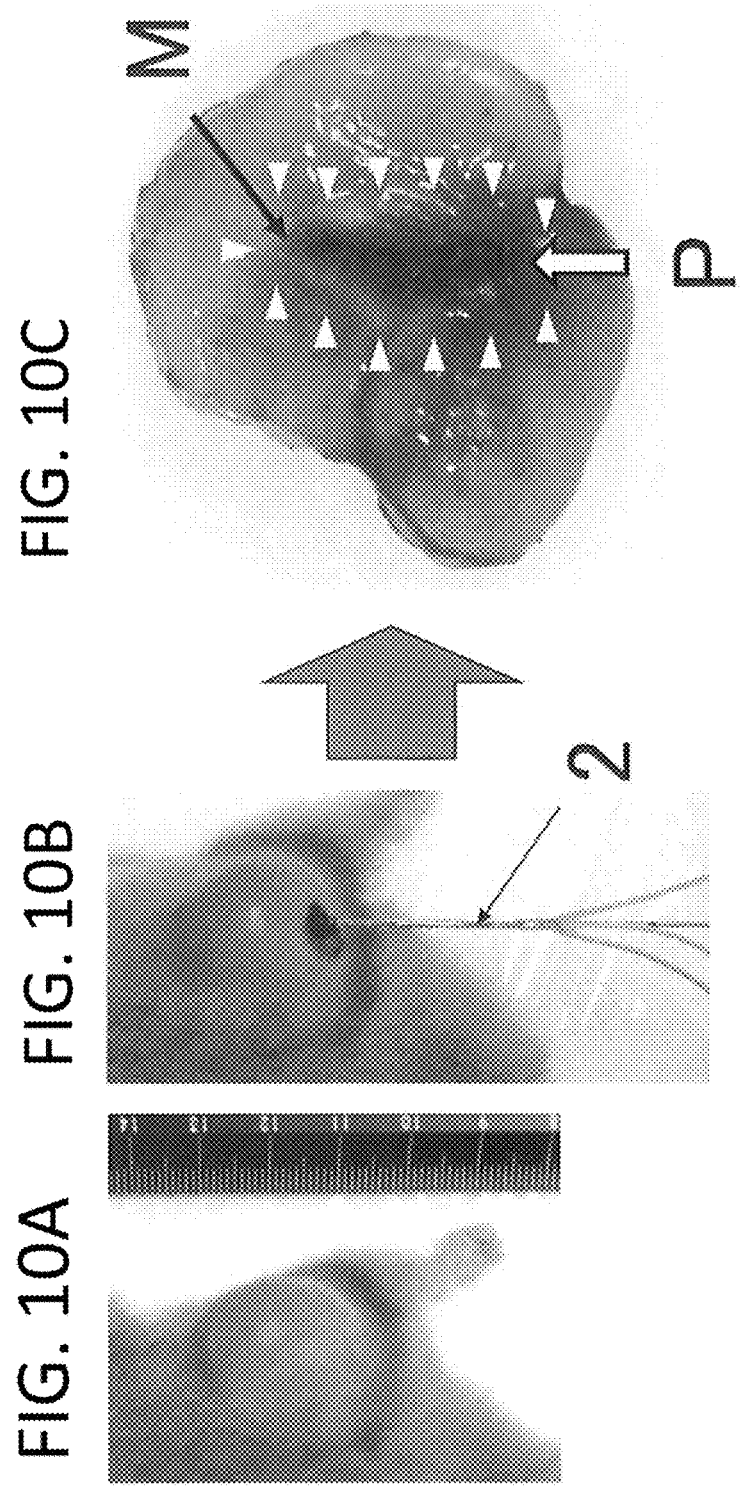

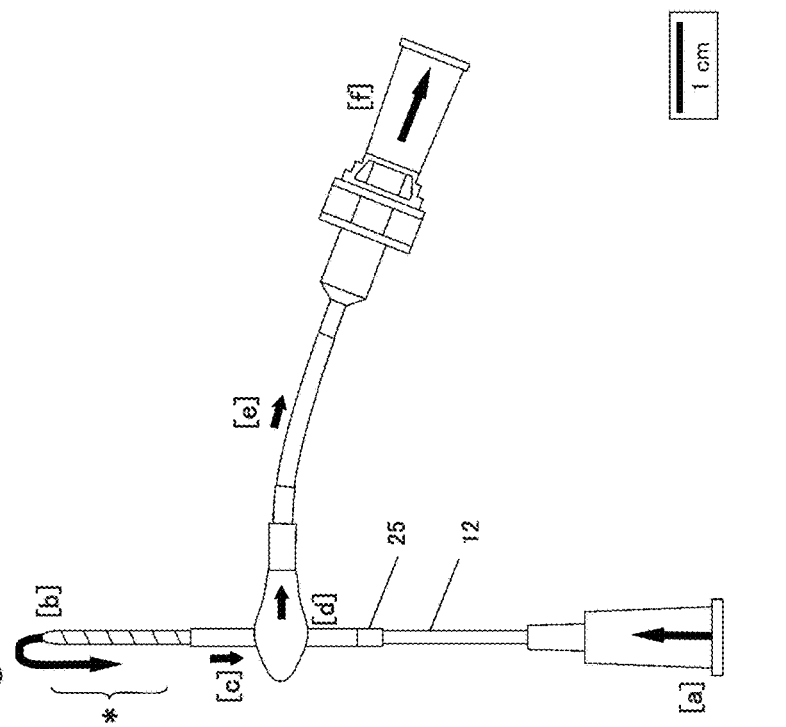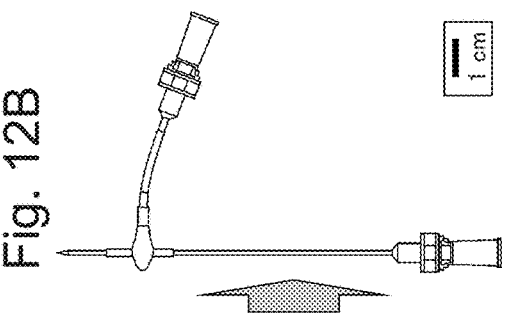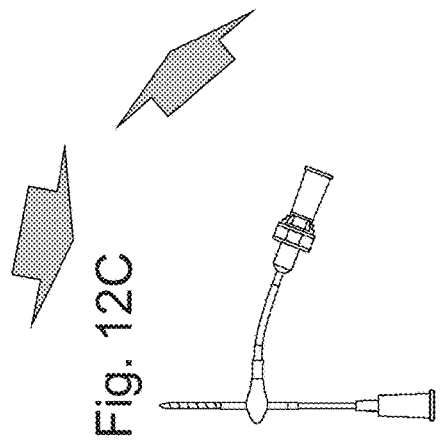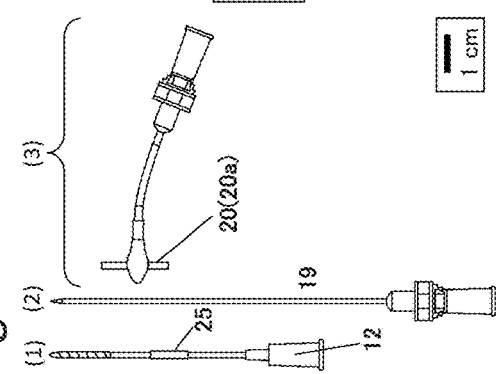

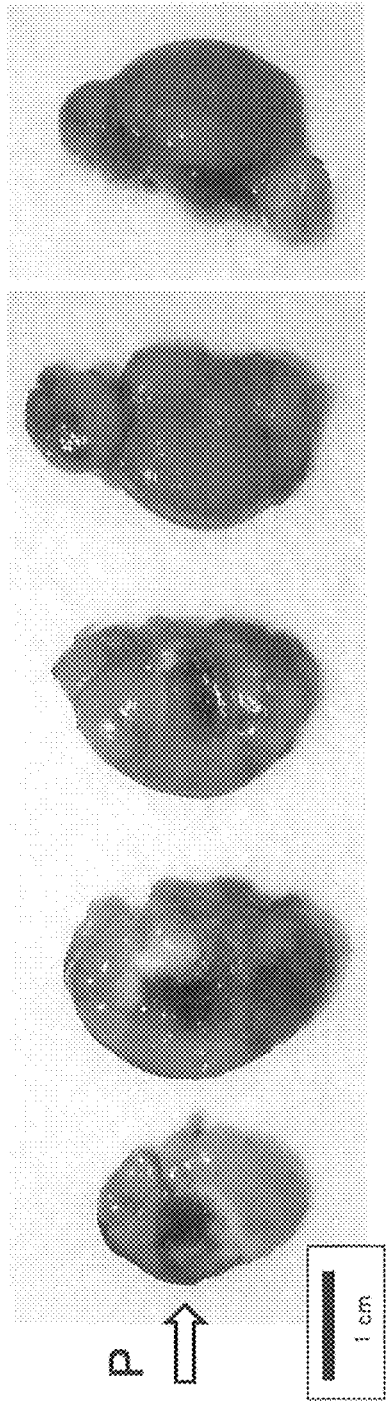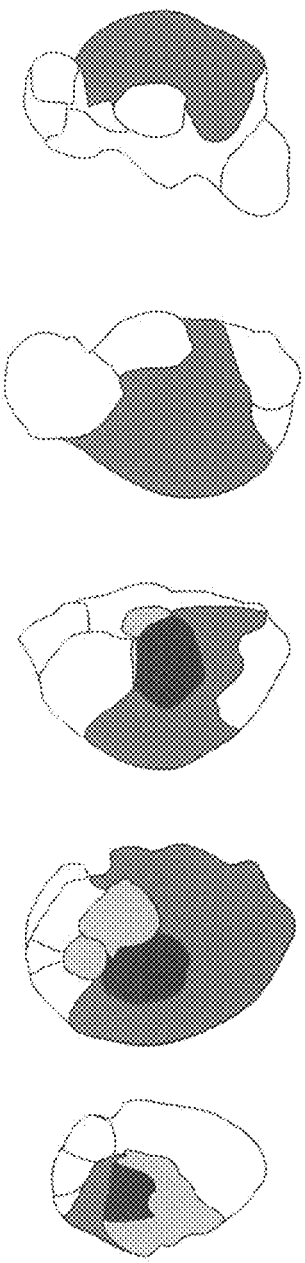
FIG. 14A
FIG. 14B

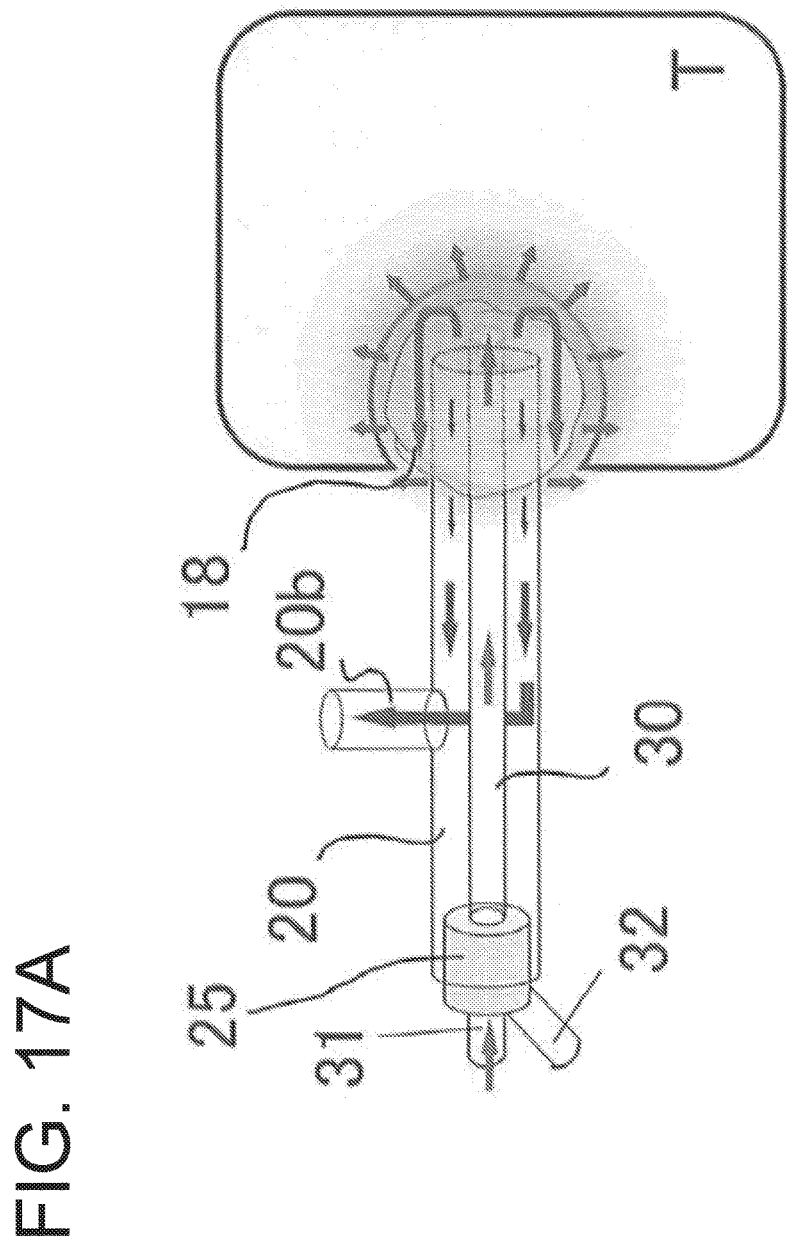

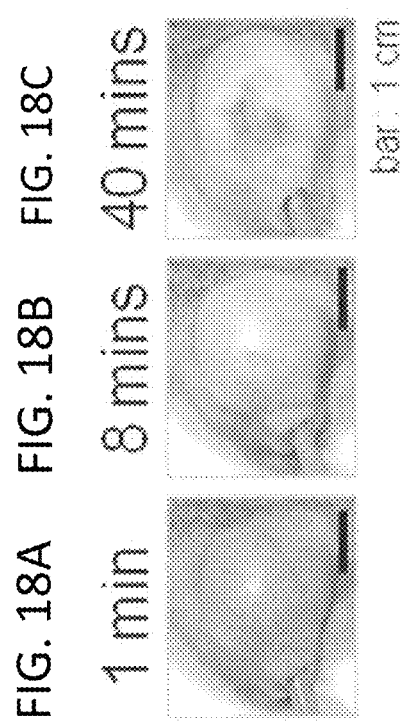
FIG. 18A 1 min  FIG. 18B 8 mins  FIG. 18C 40 mins
bar : 1 cm

APPARATUS AND SYSTEM FOR CONTROLLING PERMEATION AND DIFFUSION OF SOLUTE AND/OR SOLVENT LOCALLY

CROSS-REFERENCE TO RELATED APPLICATION

The present application claims a benefit of priority from Japanese Patent Application No. 2014-083036 filed on Apr. 14, 2014, the entirety of which is incorporated herein by reference.

TECHNICAL FIELD

The present invention relates to a permeation apparatus and a fluid injection apparatus. More specifically, the present invention relates to a permeation apparatus, a kit, and an injection apparatus for causing a fluid injected into an affected area to diffuse in the vicinity of an injection position.

DESCRIPTION OF THE RELATED ART

A large number of therapies of diseases by a drug administration method involving directly injecting a drug solution into a body tissue have been reported. It has also been reported that the permeation and diffusion of a drug into a surrounding tissue by this method involves two mechanisms of "diffusion of a substance" and "fluid convection" (U.S. Pat. No. 6,753,005 B1). The former refers to the diffusion of a substance based on the concentration gradient of the substance, and the latter refers to the convection of a drug solution to the surrounding area due to increase in pressure in a local site into which the drug solution has been injected (Proc Natl Acad Sci USA. 1994 Mar. 15; 91(6): 2076-80).

In the actual clinical setting, there has been carried out a therapeutic method involving suppressing the growth of each tumor by directly administering a drug such as an anticancer drug into a malignant brain tumor (Brain Pathol. 2013 Aug. 15. doi: 10.1111/bpa. 12082. (Epub ahead of print)) or injecting absolute ethanol or 50% acetic acid into a cancer lesion that has developed in the liver (J Hepatol. 2010 March; 52(3): 380-8). Further, in the field of urinology, a therapeutic method involving reducing the size of the prostate gland by directly injecting absolute ethanol into the prostate gland has been carried out with respect to prostatic hyperplasia (J Urol. 2007 March; 177(3): 1030-5: discussion 1035). Those therapeutic methods involving directly injecting a drug in situ have achieved certain results, but there still remain quite a number of problems in the drug administration method itself. According to the drug administration method, in principle, a drug is left in an injection site, and hence the in-situ pressure that increases suddenly in the drug injection site cannot be controlled. As a result, there arise problems such as "backflow of a drug solution to an outside through an inserted needle", "leakage of a drug solution to an unintended site", and "non-uniform spread of a drug solution" (J Neurosurg. 2007 September; 107(3): 568-77, J Urol. 2012 May; 187(5): 1898-902, J Neurosurg. 1999 February; 90(2): 315-20, Brain Pathol. 2013 Aug. 15. doi: 10.1111/bpa. 12082). Those problems have significant effects on therapeutic effects of diseases by the therapeutic methods, and thus there is a demand for solving those problems.

SUMMARY OF THE INVENTION

It is an object of the present invention to provide a permeation apparatus, a kit, and a fluid injection apparatus capable of causing a fluid to diffuse in situ in a wide range.

The inventor of the present invention considered that, in order to cause a drug to efficiently permeate and diffuse to a tissue in a local site into which a fluid such as a drug solution has been directly administered, it is important to control the in-situ pressure. Further, the in-situ pressure can be controlled by appropriately controlling the amount of the drug solution (fluid) in a local site into which the drug solution (fluid) has been injected. The inventor of the present invention achieved the present invention particularly focusing on this point.

The present invention provides the following permeation apparatus, kit, and injection apparatus.

According to the first aspect of the invention, a permeation apparatus a permeation apparatus comprising an aspiration tube; an injection tube; and a water-absorbing cover member for covering at least a distal end of the injection tube and a vicinity of the distal end is provided. The aspiration tube is configured to aspirate a fluid flowing from the water-absorbing cover member into the aspiration tube.

According to the second aspect of the invention, a permeation apparatus connected to an aspirator and an injection apparatus, for injecting and aspirating a fluid to and from a target injection site is provided. The permeation apparatus comprises an aspiration tube connectable to the aspirator; an injection tube connectable to the injection apparatus; and a tube communicating to the injection tube, for supplying air. The aspirator is configured to aspirate the fluid flowing into the aspiration tube through the aspiration tube. The air is taken into the injection tube through the tube for supplying the air at a time of the aspiration.

According to the third aspect of the invention, an in-situ permeation system comprising either of the above permeation apparatus; an aspirator connectable to the aspiration tube; and a fluid injection apparatus capable of injecting a fluid is provided. The fluid injection apparatus includes a syringe connectable to the injection tube; and at least one injection unit for injecting the fluid with the syringe through the injection tube.

BRIEF DESCRIPTION OF THE DRAWINGS

FIG. 3A is a photograph for showing a hollow tube (left) and the permeation apparatus (right) to be introduced into the hollow tube.

FIG. 3B is a photograph for showing a water-absorbing cover member after 70 µL of $H_2O$ has been injected.

FIG. 5A is a photograph for showing a state in which a 22-gauge (length: 7 cm) syringe needle is inserted by 5 mm into each water-absorbing cover member. FIG. 5B is a photograph for showing a state in which each water-absorbing cover member is immersed in 1 mL of $H_2O$. FIG. 5C is a photograph for showing a state after $H_2O$ in each water-absorbing cover member and in the surrounding area has been aspirated for 3 seconds.

FIG. 7B is a table for showing a relationship between the scale and the injection amount for each capacity of a syringe.

FIG. 8A and FIG. 8B are photographs for showing the degree of diffusion of an injected fluid.

FIG. 10A, FIG. 10B, and FIG. 10C are photographs for showing the degree of diffusion of an injection fluid in a mouse subcutaneous tumor. FIG. 10A is a photograph before treatment. FIG. 10B is a photograph immediately before the start of injection of the fluid. FIG. 10C is a photograph of a tumor section after the injection of the fluid. The arrow denoted by P indicates an insertion direction of the permeation apparatus, and the arrow denoted by M indicates a site where methylene blue has permeated.

FIG. 12A, FIG. 12B, FIG. 12C and FIG. 12D are a usage example of the permeation apparatus of FIG. 11A and FIG. 11B. FIG. 12A is an illustration of a kit configuration for the permeation apparatus: (1) an injection tube (20-gauge intravascular catheter) covered with a water-absorbing cover member; (2) a puncture needle; and (3) a fluid flowing out of a local site is removed through a 15-gauge hollow tube (aspiration tube). The hollow tube (the aspiration tube) is connected to the aspirator 3 through the connection portion.

FIG. 14A is a photograph for showing a state of diffusion of methylene blue in a tumor after the injection of the methylene blue in Example 3. The tumor is shown in sections obtained by slicing the entire tumor with a thickness of from 8 mm to 10 mm. The arrow denoted by P indicates an insertion direction of the permeation apparatus. FIG. 14B is images for illustrating the sections of FIG. 14A through color coding. A site that a solute and/or a solvent has permeated and diffused to in this experiment is classified into three colored-sites, and an uncolored white site indicates a site that neither the solute nor the solvent has permeated and diffused to.

FIG. 15D is images for illustrating the tumor sections of FIG. 15B through color coding. A site where a solute and/or a solvent has permeated and diffused in this experiment is classified into three colored-sites, and an uncolored white site indicates a site that neither the solute nor the solvent has permeated and diffused to.

FIG. 16A is an example of an exploded view. FIG. 16B is an enlarged view of the water-absorbing cover member at the distal end of the permeation apparatus. FIG. 16C is a view of the assembled permeation apparatus. FIG. 16D is an enlarged end surface view of a proximal end of a connector.

FIG. 17A is another example of the distal end of the permeation apparatus.

FIG. 18A to FIG. 18C are photographs for showing a change with time in size of a tumor.

DETAILED DESCRIPTION OF THE PREFERRED EMBODIMENTS

As a fluid to be diffused in the present invention, there is given a fluid in which a pharmaceutical product is dissolved. There is no particular limitation on the pharmaceutical product as long as the pharmaceutical product can be injected as an injection solution, and a wide range of pharmaceutical products, in particular, an anticancer drug can be used. The fluid may contain a graft material such as iPS cells or stem cells. Further, the fluid may have any form such as a solution, a suspension, or an emulsion.

The fluid to be injected in the present invention diffuses widely from an injection site to the surrounding area, and hence the present invention is suitable for an application of supplying a fluid containing a pharmaceutical product or the like at a high concentration to a particular site.

First to third embodiments of the present invention are described with reference to the drawings.

First Embodiment

Figure 1:
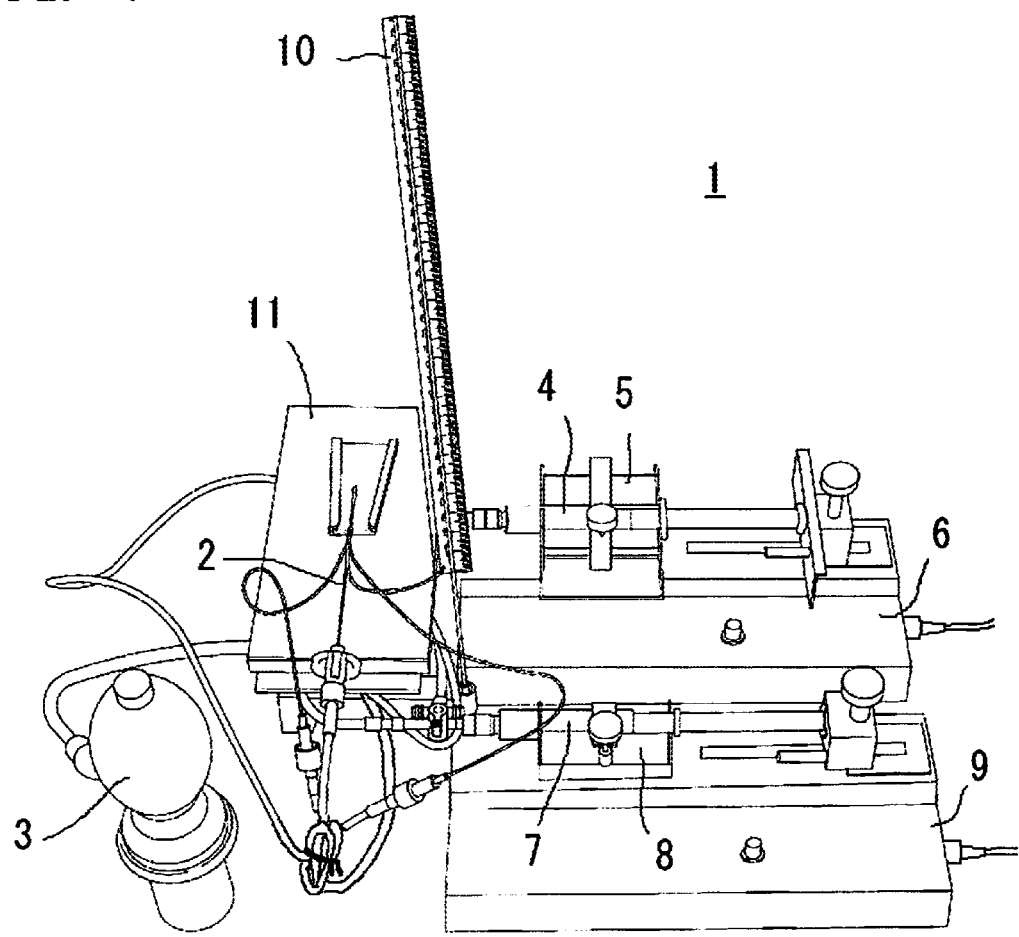
FIG. 1 is an illustration of an entire apparatus of the present invention.

FIG. 1 is an illustration of an entire image of a fluid injection apparatus 1 of the present invention serving as an in-situ permeation system. The injection apparatus 1 includes a permeation apparatus 2, an aspirator 3, a first fixing device 5 for fixing a first syringe 4, a microsyringe pump serving as a first injection unit 6 for feeding a fluid to the first syringe 4, a second fixing device 8 for fixing a second syringe 7, a microsyringe pump serving as a second injection unit 9 for feeding a fluid to the second syringe 7, a cavity pressure meter 10 as an optional component, and a tissue table 11 for placing an injection target thereon. Although the two syringes 4 and 7 are respectively fixed by the two fixing devices 5 and 8 in FIG. 1, one syringe or three or more syringes may be used. In the case where a plurality of syringes are fixed, fluids in the respective syringes may be the same or may be different from each other.

It should be noted that, although the first syringe 4 and the second syringe 7 are fixed by the first fixing device 5 and the second fixing device 8 in this embodiment, the members in addition to the syringes or the members other than the syringes may be fixed by the fixing devices. For example, the in-situ permeation system may include a fixing device for fixing at least one of the first and second syringes 4 and 7, the permeation apparatus 2, the aspirator 3, a pressure application device such as a syringe 44 (described later), or a pressure meter such as the cavity pressure meter 10 or a pressure measurement device 41 (described later). In particular, the fixing device fixes at least one of the first and second syringes 4 and 7, the permeation apparatus 2, the aspirator 3, the pressure application device, or the pressure meter integrally to the in-situ permeation system. By bringing the in-situ permeation system including those members into a room of a patient, a tumor regression therapy using the in-situ permeation system can be carried out relatively easily over a long period of time even in the room of the patient instead of an operation room.

As the aspirator 3, the syringes 4 and 7, the injection units 6 and 9, the cavity pressure meter 10, and the tissue table 11, known devices may be used. As the aspirator 3, for example, there is given an MMI manual aspirator manufactured by Muranaka Medical Instruments Co., Ltd. As the syringes 4 and 7, for example, there is given 1005TLL 5 ML SYR manufactured by Hamilton Company. As the injection units 6 and 9, for example, there is given a series of microsyringe pumps manufactured by AS ONE Corporation. As the cavity pressure meter 10, a cavity pressure meter calibrated in 1 cm up to a height of 27 cm is illustrated.

Figure 2:
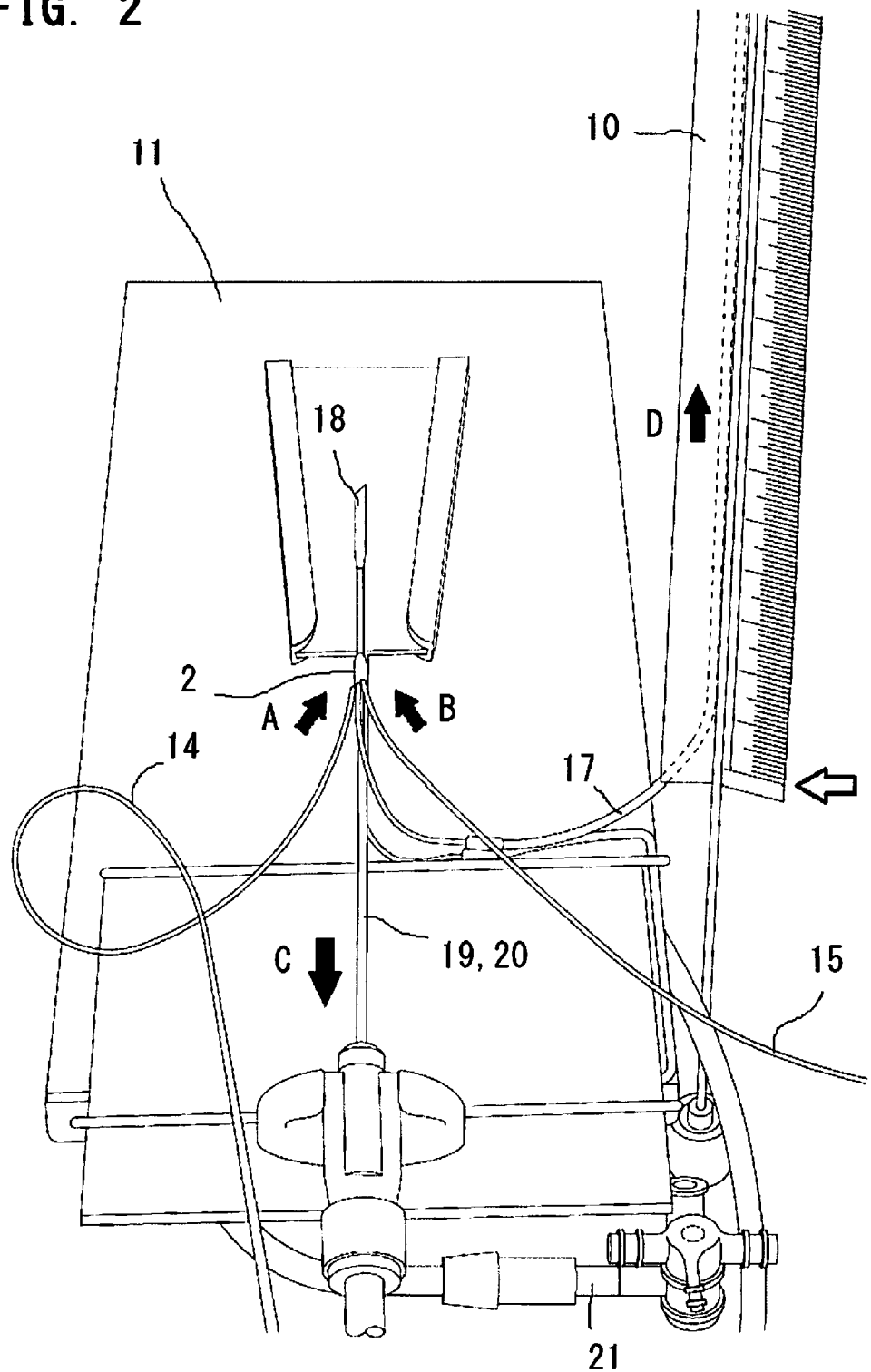
FIG. 2 is an illustration of a cavity pressure meter and a permeation apparatus provided in the apparatus of the present invention.

FIG. 2 is an illustration of the permeation apparatus 2 and the cavity pressure meter 10. The tissue table 11 is designed to be small assuming the case where the arm, the hand, the fingertip, or the like is to be an injection site in FIG. 2. However, a larger table may be used in the case where the leg, the arm, the organ, or the like is to be the injection site, or a bed on which a patient lies down may be used. Plungers of the first syringe 4 and the second syringe 7 are connected to corresponding injection tubes 12 and 13 (FIG. 4) of the permeation apparatus 2 through tubes 14 and 15, respectively, and the cavity pressure meter 10 is connected to a cavity pressure tube 16 (FIG. 4) of the permeation apparatus 2 through a tube 17. Fluids pushed out of the first syringe 4 and the second syringe 7 by the first injection unit 6 and the second injection unit 9 are injected into an injection site of the organ, the tissue, or the like through the injection tubes 12 and 13 of the permeation apparatus 2 (arrows A and B). In FIG. 2, a distal end of the permeation apparatus 2 is covered with a water-absorbing cover member (PVA) 18. It should be noted that the injection tubes 12 and 13 and the cavity pressure tube 16 can be manufactured through use of known syringe needles (for example, 18-gauge (outer diameter: 1.20 mm) to 32-gauge (outer diameter: 0.26 mm) needles) or the like.

The arrows of FIG. 2 indicate movement directions of a fluid. The fluid flows from an aspiration tube 20 of the permeation apparatus 2 to the aspirator 3 (FIG. 1) through a tube 21, and thus a sudden increase in pressure in an in-situ cavity can be prevented. The water-absorbing cover member 18 is used for both purposes of diffusing an injected fluid and aspirating a body fluid in the vicinity of the injection site. The water-absorbing cover member 18 can also serve as a filter for preventing the permeation of blood and insoluble supermolecules such as cells or cellular fragments into the inside at the injection site. It should be noted that the aspiration tube 20 can be manufactured through use of a known syringe needle (for example, 18-gauge (outer diameter: 1.20 mm) to 32-gauge (outer diameter: 0.26 mm) needles) or the like.

When fluids are injected in situ through the injection tubes 12 and 13, a pressure increases in situ, and then the pressure is measured with the cavity pressure meter 10. A medical worker such as a nurse may adjust the injection rates of the fluids by operating the injection rates of the first injection unit 6 and the second injection unit 9 while monitoring the pressure indicated by the cavity pressure meter 10. Alternatively, the pressure in the fluid injection site can also be automatically maintained in a predetermined range by transmitting pressure data from the cavity pressure meter 10 as a signal to a control device such as a CPU, thereby controlling the first injection unit 6 and the second injection unit 9 with the control device. The pressure in the fluid injection site may be a zero pressure or a negative pressure, and may be a predetermined pressure as long as a fluid does not leak from the injection site. In one embodiment, the pressure can also be set to a negative pressure constantly during an in-situ permeation (ISP) operation. The numerical value of the pressure varies also depending on an injection site (for example, the subcutaneous part, the muscle, the organ, etc.), and hence can be appropriately set in accordance with the injection site. A fluid from an injection local site and/or a body fluid can flow into the cavity pressure tube 16, and the cavity pressure tube 16 can also serve as a space allowing a fluid (body fluid), which has no place to go, to flow therein (pass therethrough). Thus, it can be monitored smoothly that an in-situ cavity is filled with the fluid. Further, as a result, a sudden increase in pressure in an in-situ cavity can be prevented. Further, the PVA serves as a seal to prevent the tubes from being clogged with blood and the like. In FIG. 2, the height of a surface at which a distal end of the cavity pressure meter 10 within the PVA was located was set to "0" cm (indicated by a white arrow).

Figure 4:
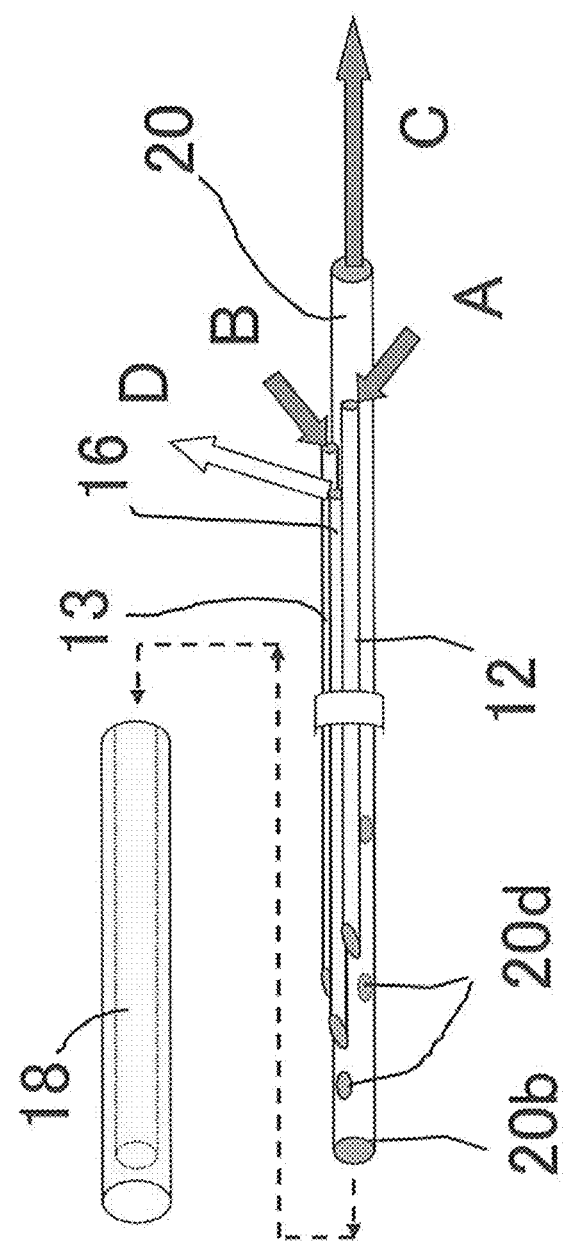
FIG. 4 is an exploded perspective view for illustrating the permeation apparatus of the present invention. Flows of a fluid denoted by arrows A to D correspond to those denoted by the arrows A to D of FIG. 2.

The pressure in the injection site can be adjusted by adjusting the injection rates of the fluids with the first injection unit 6 and the second injection unit 9 and aspirating and removing a fluid or a body fluid in the injection site with the aspirator 3. The aspirator 3 is connected to the aspiration tube 20 and aspirates a body fluid in the injection site of a fluid, a body fluid, a lymph fluid, blood, or the like or on the periphery thereof through an opening of a distal end 20b of the aspiration tube 20 and at least one small hole 20d (FIG. 4). The aspiration of the body fluid and the like by the aspirator 3 may be performed continuously or may be performed intermittently depending on the pressure. The in-situ aspiration of the fluid by the aspirator 3 can prevent a sudden increase in pressure in an in-situ cavity. Further, the water-absorbing cover member (PVA) 18 serves as a seal to prevent the tubes from being clogged with blood and the like. Further, the aspiration of the body fluid and the like by the aspirator 3 provides a space allowing a fluid (body fluid), which has no place to go, to flow therein (pass therethrough).

As shown in FIG. 3A and FIG. 3B and illustrated in FIG. 4, the permeation apparatus 2 according to one embodiment to be used in the present invention includes the aspiration tube 20, the injection tubes 12 and 13, the cavity pressure tube 16, and the water-absorbing cover member 18 covering distal ends of the aspiration tube 20, the injection tubes 12 and 13, and the cavity pressure tube 16 and the vicinity thereof. The aspiration tube 20, the injection tubes 12 and 13, and the cavity pressure tube 16 are integrally fixed. The permeation apparatus 2 may be mounted on the injection apparatus 1 or may be provided separately from the injection apparatus 1 and mounted thereon at a time of the injection of a fluid. It should be noted that the "vicinity thereof" in the description "distal end and vicinity thereof" refers to an area adjacent to the distal end. The length of such an area in a longitudinal direction varies for each member and ranges generally from 0.1 mm to 5 cm, more preferably from 1 mm to 3 cm.

Figure 6A:
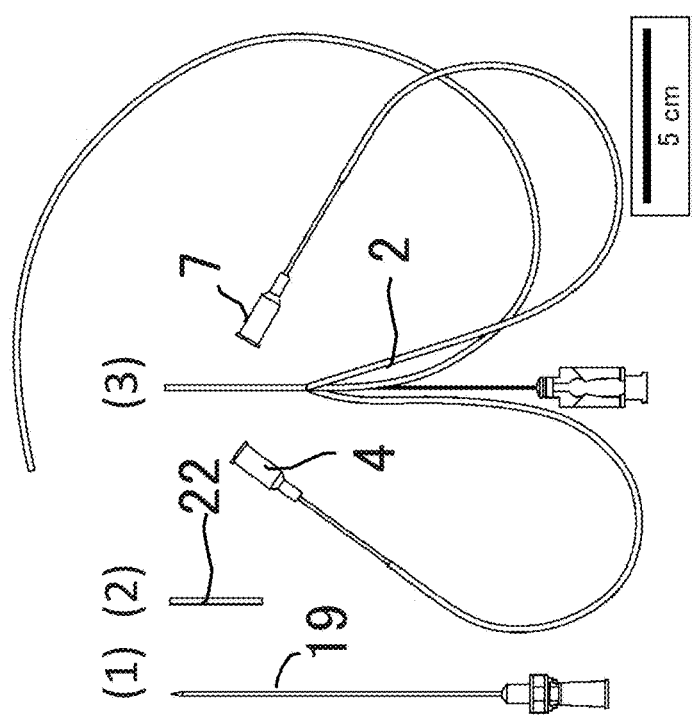
FIG. 6A is a photograph for showing respective parts of the permeation apparatus: (1) a puncture needle; (2) a 15-gauge hollow tube; and (3) the permeation apparatus of FIG. 3B inserted in the hollow tube.
Figure 6B:
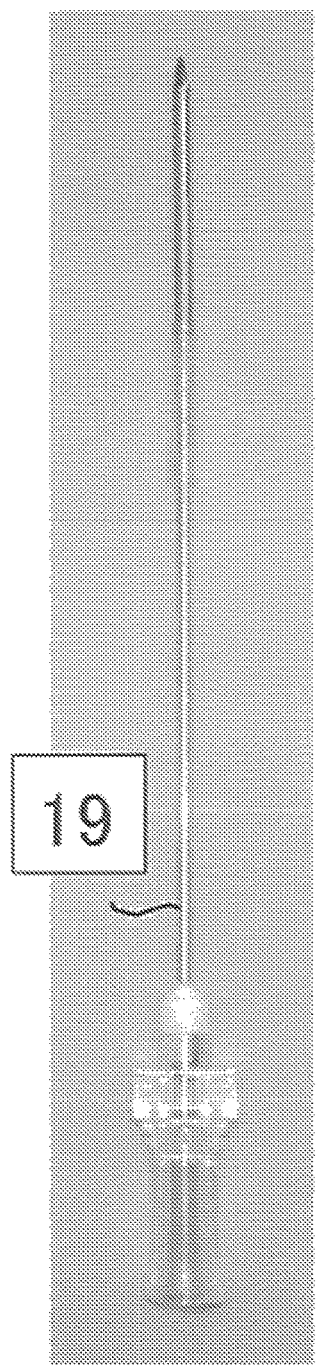
FIG. 6B, FIG. 6C, FIG. 6D, and FIG. 6E are photographs showing procedures 1 to 4, respectively, for inserting a distal end of the permeation apparatus into a tissue and introducing a fluid into the tissue.
Figure 6C:
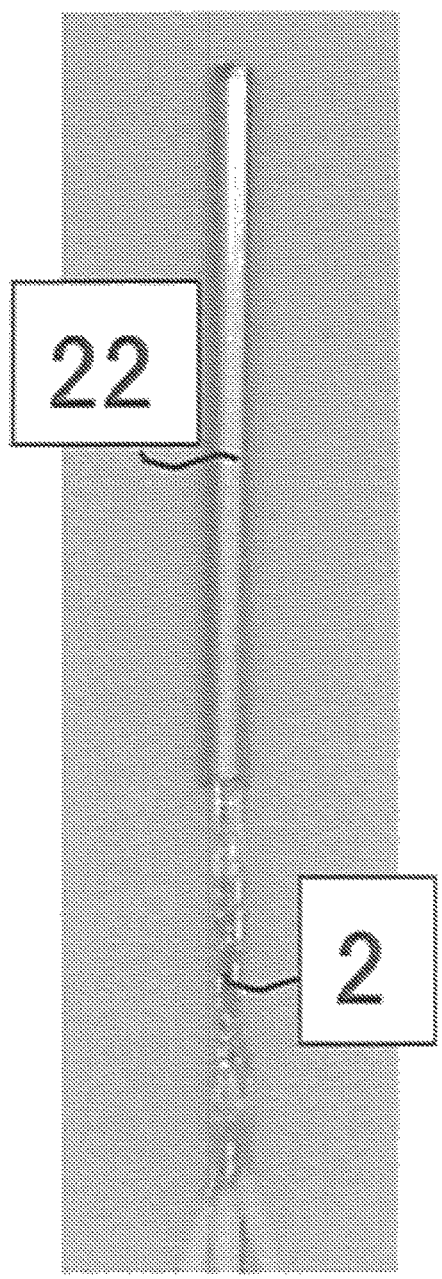

The permeation apparatus 2 can be mounted on the injection apparatus 1 through the connection between the aspiration tube 20 and the aspirator 3, the connection between the injection tubes 12 and 13 and the first syringe (plunger) 4 and the second syringe (plunger) 7, and the connection between the cavity pressure tube 16 and the cavity pressure meter 10. Those connections can be performed through use of the tube 21, the tubes 14 and 15, and the tube 17 each having an appropriate diameter. The permeation apparatus 2 is sized to be inserted in a hollow tube 22 as shown in FIG. 3A and is introduced into the injection site through the hollow tube 22 (FIG. 6C). There is no particular limitation on the dimensions of the hollow tube 22, and for example, a 15-gauge (outer diameter: 1.83 mm, inner diameter: 1.63 mm) metallic tube can be used. In another embodiment, the hollow tube 22 is a hollow member (outer diameter: 3 mm, inner diameter: 2.5 mm) made of polypropylene.

Figure 5A:
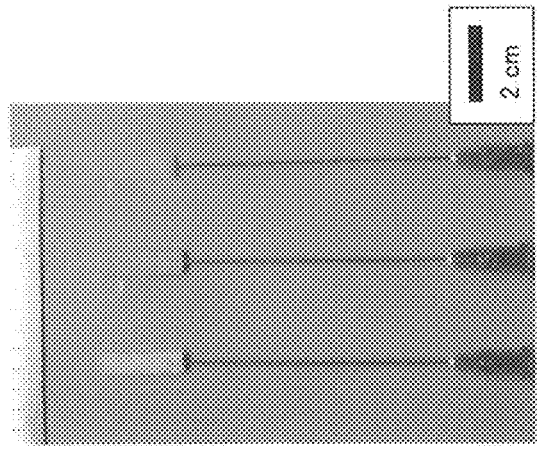
FIG. 5A, FIG. 5B, and FIG. 5C are photographs for showing examples of water-absorbing cover members made of different water-absorbing materials (1: polyvinyl alcohol (PVA), 2: 80% rayon and 20% polyester, and 3: melamine foam). Each example has a width of 5 mm, a length of 20 mm, and a thickness of 1.5 mm.
Figure 5B:
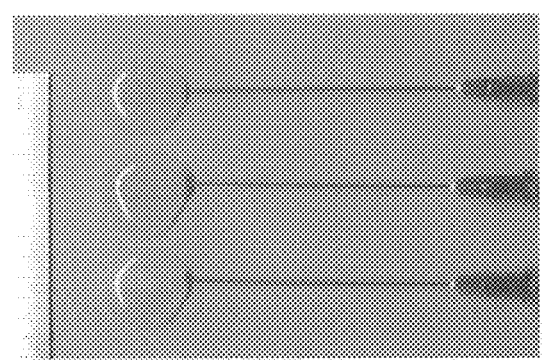
Figure 5C:
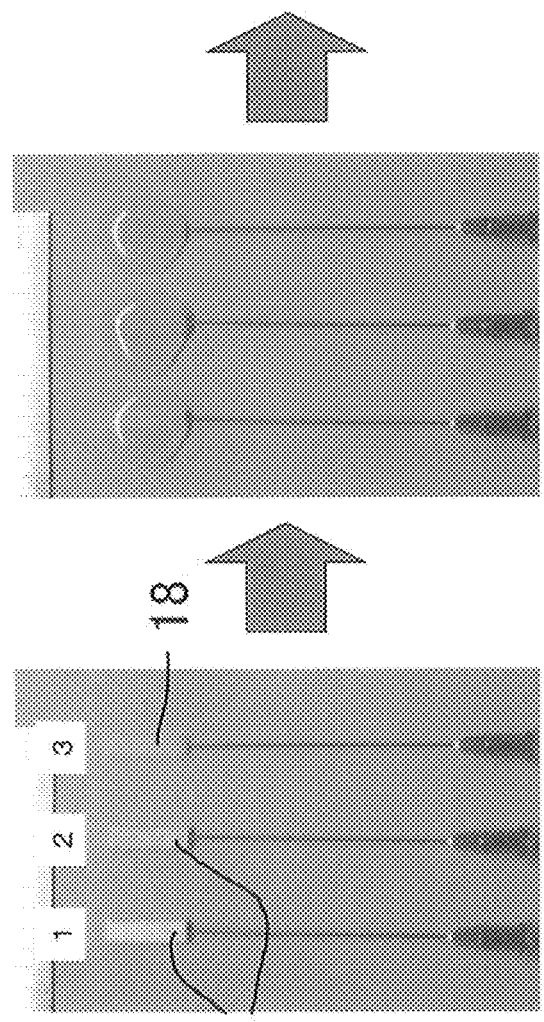

It is preferred that a fluid be injected through the permeation apparatus 2 because the fluid diffuses from the entire water-absorbing cover member 18 as shown in FIG. 5A to FIG. 5C. It is preferred that the water-absorbing cover member 18 be made of a material such as PVA having characteristics of allowing the fluid to "permeate more uniformly and thereafter exude more uniformly". As shown in FIG. 5A to FIG. 5C, when three types of the water-absorbing cover members 18 (FIG. 5A) are immersed in a fluid (FIG. 5B), the water-absorbing cover member 18 can absorb the surrounding fluid more effectively, and also draw and absorb the fluid located farther away (in a deep portion) (FIG. 5C) due to the strong water-absorbing capability. As a result, the fluid in the surrounding tissue can be removed more efficiently by aspiration (through the aspiration tube illustrated in FIG. 2).

It is appropriate that the water-absorbing cover member 18 be made of a material capable of absorbing and retaining a fluid such as a body fluid. The water-absorbing cover member 18 may be made of a hydrophilic polymer, a foam capable of retaining an aqueous fluid such as a body fluid, a knitted and woven fabric or a nonwoven fabric containing water-absorbing fibers, or the like. Examples of the hydrophilic polymer include polyvinyl alcohol (PVA), polyethylene glycol, polyvinylpyrrolidone (PVP), methylcellulose, ethylcellulose, hydroxypropylmethylcellulose, carboxymethylcellulose, chitosan, and agarose. Examples of the foam include melamine resin foam, polyurethane foam, polystyrene foam, polyolefin foam, phenol resin foam, polyvinyl chloride (PVC) foam, urea resin (UF) foam, silicone (SI) foam, and polyimide (PI) foam. Examples of the water-absorbing fibers include rayon, cotton, linen, and wool. The water-absorbing cover member 18 can retain a fluid therein by being made of a combination of the above-mentioned water-absorbing fibers and fibers having small water-absorbing property (polyester, etc.). The water-absorbing cover member 18 can retain a fluid therein and is fixed to the permeation apparatus 2 so as to cover a distal end thereof.

Figure 6D:
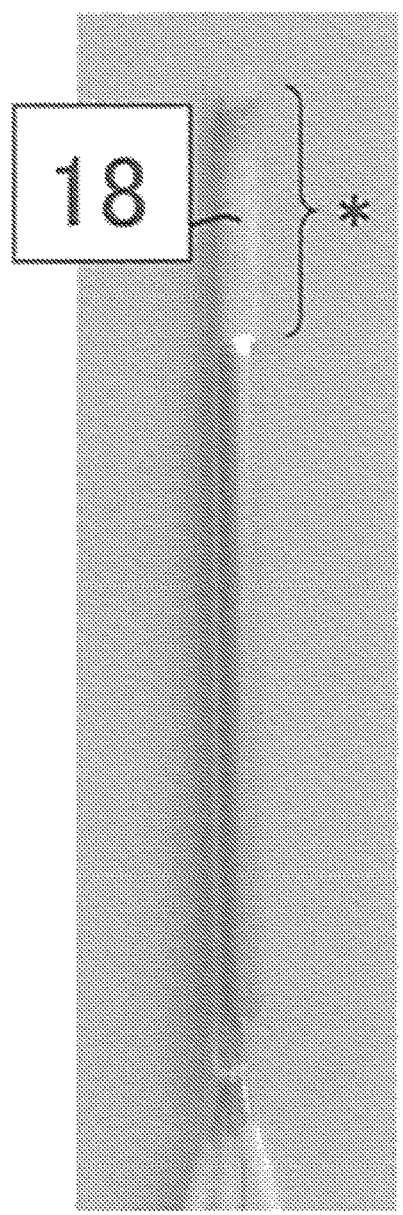
Figure 6E:
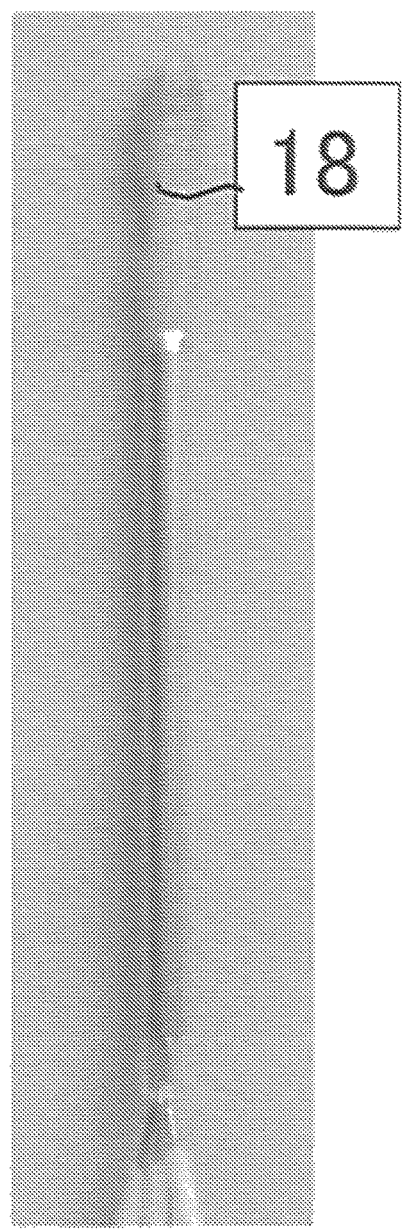

The permeation apparatus 2 cannot be directly inserted or retained in a living body. Therefore, as shown in FIG. 6A, a puncture needle 19 is inserted into a target tissue in such a state that a distal end of the puncture needle 19 is covered with the cylindrical hollow tube 22. Then, the puncture needle 19 is pulled out of the tissue, and the permeation apparatus 2 is inserted into the hollow tube 22 (FIG. 6B). After that, only the hollow tube 22 is pulled out of the tissue without moving the permeation apparatus 2 (FIG. 6C), and intended fluids are injected into the tissue with the syringe 4, 7 (FIG. 6D). In this case, the injected fluids are absorbed by the water-absorbing cover member 18 (FIG. 6E) and gradually diffuse from an injection site.

Figure 7A:
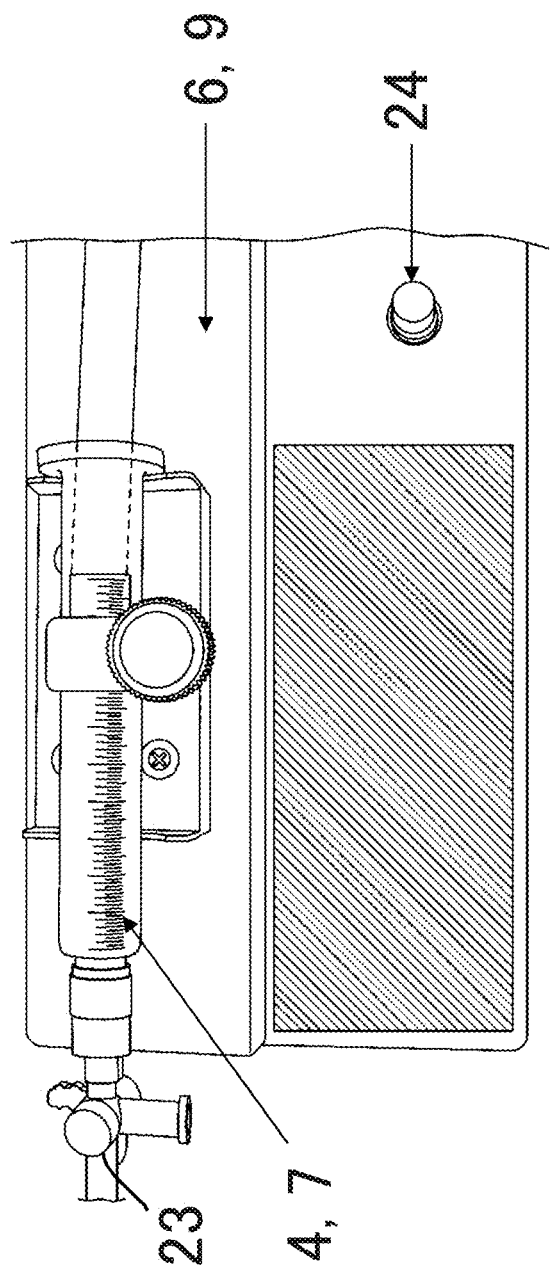
FIG. 7A is a photograph for showing the control of an injection rate and an injection amount by an injection unit.

A relationship between the injection amount and the injection rate of the fluids from the syringe 4, 7 is shown in FIG. 7B. In FIG. 7A, the injection amount is adjusted by rotating a scale 24, and a three-way cock 23 is fixed to the syringe 4, 7 to control the injection of the fluids from the syringe 4, 7. FIG. 7B is a table for showing a relationship between the scale and the injection amount for each capacity of the syringes.

According to a related-art convection-enhanced delivery (CED) method, increase in pressure occurs in a local site into which a fluid has been injected, and the fluid leaks. However, according to the first embodiment of the present invention, the diffusion of the fluid in a wide range can be realized by suppressing an in-situ pressure to a predetermined value or less while monitoring the pressure. The in-situ pressure may be in the vicinity of 0, and the permeation and diffusion of the fluid can also be performed in such a state that the in-situ pressure is increased and controlled. In addition, according to the present invention, defects of the CED method, that is, "the permeation and diffusion of a solute and/or a solvent are liable to be influenced by the state of a target tissue and various elements of an injection method and are difficult to control" and "the backflow of a solute and/or a solvent through a puncture needle, or the leakage and spread thereof to an unintended site" can be prevented.

What is important in the present invention is that the aspirator can aspirate a perfusion fluid containing a fluid derived from a target tissue (exuding from the target tissue) from an in-situ cavity as needed. Thus, an undiluted thick fluid can be supplied to the in-situ cavity as needed. Further, as a result, fluid components contained in the target tissue can be removed from the target tissue, and thus the permeation property and diffusion property of the fluid in the in-situ tissue can be enhanced. This also cannot be achieved in the conventional CED method.

Further, in the present invention, several kinds of fluids are allowed to permeate and diffuse to a target tissue in one treatment. For example, in the case of using the permeation apparatus 2 shown in FIG. 3A and FIG. 3B, the permeation and diffusion of two kinds of fluids can be performed by simultaneous injection or alternate injection. Further, the simultaneous permeation and diffusion of three or more kinds of fluids can be realized more easily by increasing the number of the injection tubes.

Second Embodiment

Figure 11A:
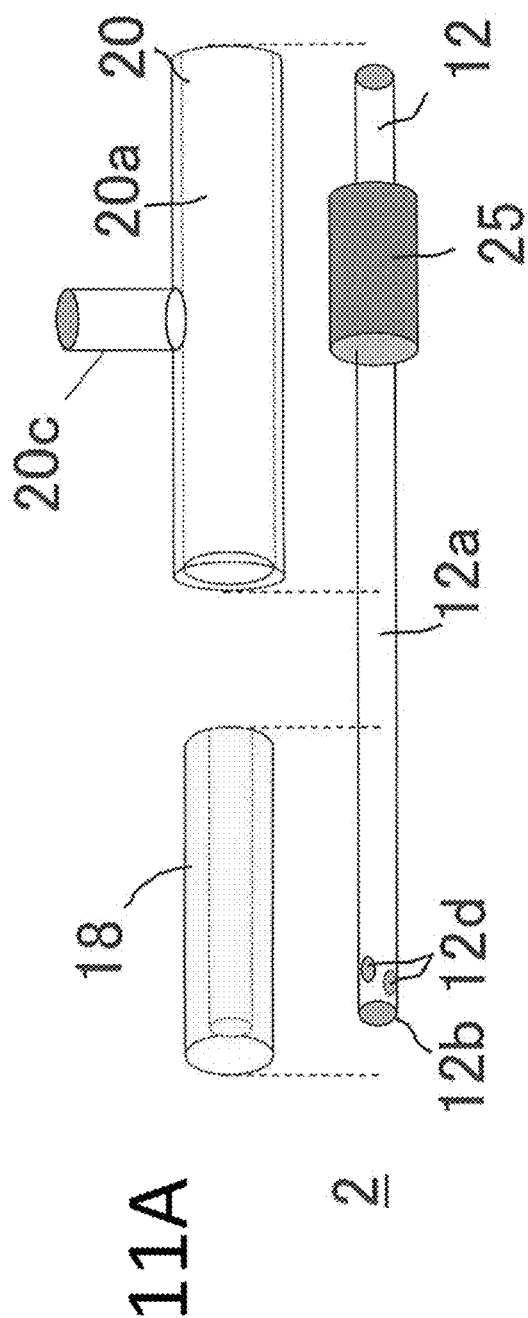
FIG. 11A is a schematic exploded perspective view of an in-situ permeation (ISP) system based on the permeation apparatus.
Figure 11B:
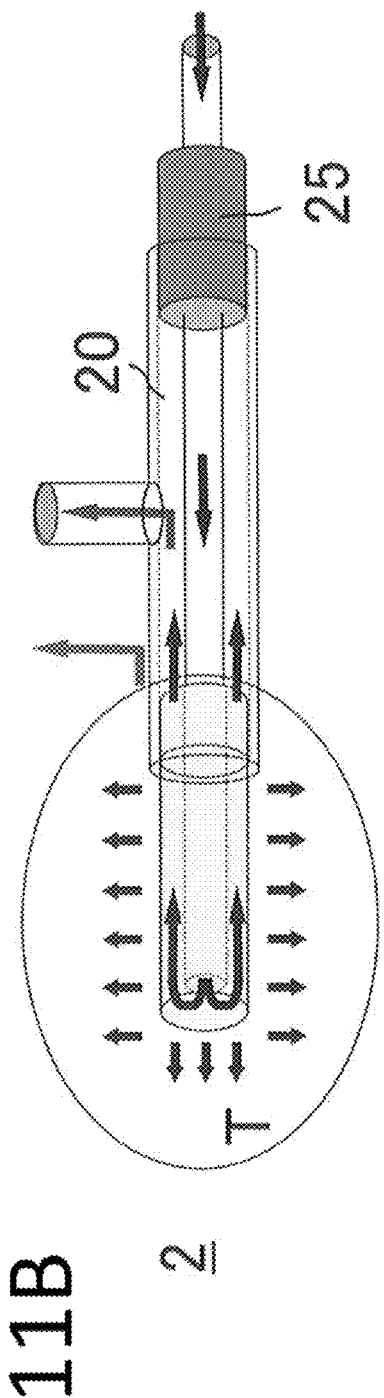
FIG. 11B is a schematic perspective view of the assembled in-situ permeation system of FIG. 11A.

FIG. 11A and FIG. 11B are illustrations of a permeation apparatus according to a second embodiment that is a preferred embodiment of the permeation apparatus of the present invention. The permeation apparatus 2 of FIG. 11A and FIG. 11B includes the aspiration tube 20, the injection tube 12, and the water-absorbing cover member 18, and a distal end 12b of the injection tube 12 is covered with the water-absorbing cover member 18. The injection tube 12 is internally fitted in an aspiration tube main body 20a with a fitting portion 25 having a diameter larger than an injection tube main body 12a, and thus a fluid is prevented from leaking to an outside from the injection unit 6 side (right side in FIG. 11A and FIG. 11B) of the aspiration tube main body 20a. It is preferred that a distal end of the injection tube 12 have a plurality of small holes 12d, and a fluid supplied through the small holes 12d permeates and diffuses into a tissue through the water-absorbing cover member 18. A part of the water-absorbing cover member 18 is inserted into the aspiration tube main body 20a on the distal end 12b side of the injection tube 12. The aspiration tube 20 includes the aspiration tube main body 20a and a connection portion 20c to be connected to the aspirator 3. When a fluid is injected from the injection tube 12, the fluid is released to diffuse to an outside from a distal end and a side surface of the water-absorbing cover member 18. In this case, when the pressure in the injection tube 12 on the distal end increases along with the injection of the fluid, the fluid containing a body fluid is released from the aspiration tube main body 20a of the water-absorbing cover member 18 to a space between the aspiration tube main body 20a and the injection tube 12 and removed by the aspirator 3 through the connection portion 20c of the aspiration tube 20. Thus, an intended solute and solvent is allowed to permeate and diffuse to a target tissue T from the injection unit 6 through the injection tube 12 and the water-absorbing cover member 18. In addition, an excessive increase in pressure in a local site can be suppressed by aspirating and removing an unnecessary fluid from the connection portion 20c of the aspiration tube 20 connected to the aspirator 3 through the tube 21. Further, the diffusion of an injected fluid to the surrounding area is accelerated by supplying a fresh fluid constantly.

FIG. 12A to FIG. 12D are a usage example of the permeation apparatus 2 of FIG. 11A and FIG. 11B, that is, an assembly kit for the permeation apparatus 2. The assembly kit for the permeation apparatus 2 includes (1) the injection tube 12 covered with the water-absorbing cover member 18; (2) the puncture needle 19; and (3) the 15-gauge hollow tube (aspiration tube 20 for removing a fluid flowing out of a local site through the aspiration tube) (FIG. 12A). The aspiration tube 20 is connected to the aspirator 3 through the connection portion 20c that comprises a small hole. A fluid passing through a space in the hollow tube and outside of the injection tube 12 can be removed by aspiration through the connection portion 20c.

The water-absorbing cover member 18 is obtained by wrapping a nonwoven fabric made of rayon and polyester and fixing the nonwoven fabric with a ligature for a surgical operation. An intended fluid permeates and diffuses to a tissue from the water-absorbing cover member 18.

The use procedure of the assembly kit is as follows. The puncture needle 19 is inserted into the aspiration tube main body 20a, and the distal end of the puncture needle 19 is inserted into the injection site (FIG. 12B). It is desired that a part of the aspiration tube main body 20a be inserted into a living body together with the puncture needle 19 because the leakage of a fluid can be suppressed. The fitting portion 25 of the injection tube 12 is closely fitted in the aspiration tube main body 20a so as to prevent the leakage of the fluid. Then, the puncture needle 19 is pulled out, and the injection tube 12 covered with the water-absorbing cover member 18 is inserted into the living body along an insertion path of the puncture needle 19 (FIG. 12C). In this case, the injection tube 12 covered with the water-absorbing cover member 18 shown in (1) of FIG. 12A can be inserted into the living body easily to the extent that the puncture needle 19 shown in (2) of FIG. 12A has been inserted into the living body.

Next, the water-absorbing cover member 18 at the distal end of the permeation apparatus 2 is set in the tissue with an intended length (length: 12 mm in this case), and about 2 mm of the water-absorbing cover member 18 on the proximal end is tightly covered with a distal end portion of the hollow tube (aspiration tube) 20. In addition, the distal end of the fitting portion 25 shown in (1) of FIG. 12A is tightly covered with a proximal end of the hollow tube (aspiration tube 20) shown in (3) of FIG. 12A. Thus, the permeation apparatus 2 can be obtained (FIG. 12D), and a fluid flow (perfusion) a-f can be realized. Further, the aspirator 3 performs aspiration appropriately to adjust the fluid so that the fluid does not leak to an outside from the tissue insertion site of the permeation apparatus 2. The permeation apparatus 2 may be assembled during a procedure for injecting a fluid into a living body through use of the assembly kit.

Third Embodiment

Next, a permeation apparatus according to a third embodiment that is an exemplary embodiment of the permeation apparatus of the present invention is described with reference to FIG. 16A to FIG. 16D. It should be noted that the same members as those of the first and second embodiments are denoted by the same reference symbols, and the descriptions of the same members are omitted. FIG. 16C is a view of the assembled permeation apparatus 2 of FIG. 16A.

Figure 16A:
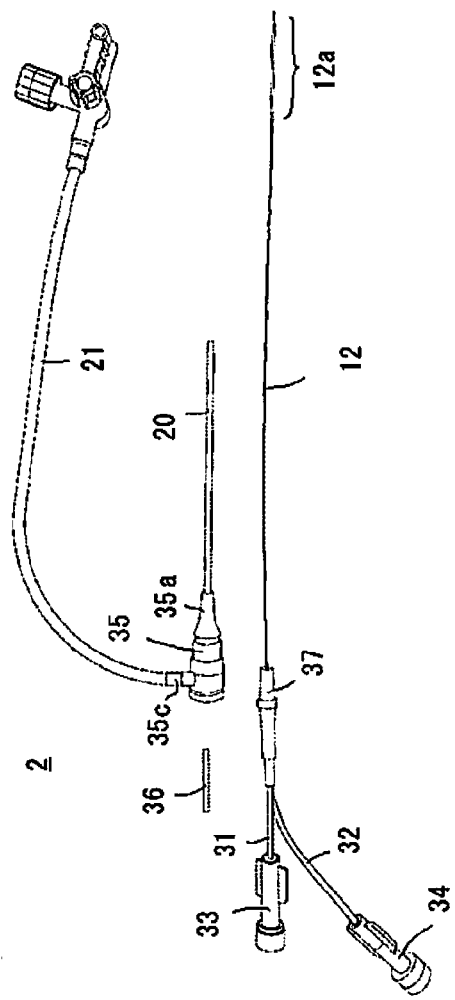
FIG. 16A, FIG. 16B, FIG. 16C and FIG. 16D are schematic views of the permeation apparatus.
Figure 16B:
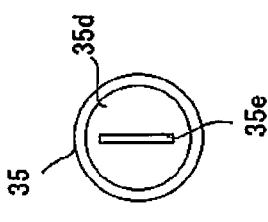
Figure 16C:
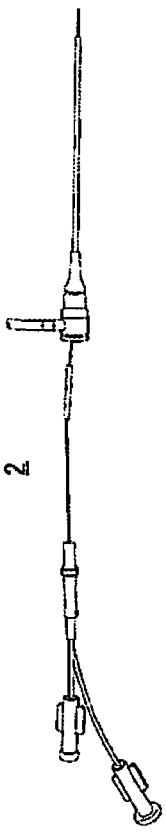

As illustrated in FIG. 16A and FIG. 16B, the permeation apparatus 2 according to the third embodiment serving as a perfusion catheter includes the aspiration tube 20 as an outer tube and the injection tube 12, and the distal end 12b of the injection tube 12 is covered with the water-absorbing cover member 18. The water-absorbing cover member 18 is made of cotton in this embodiment. The water-absorbing cover member 18 is wrapped around an outer peripheral surface of the distal end 12b of the injection tube 12, and the proximal end of the water-absorbing cover member 18 is placed in the aspiration tube 20.

Distal ends of two tubes 31 and 32 are connected to a proximal end of the injection tube 12 through a connector 37. A proximal end of the tube 31 is connected to a fluid injection channel 33. The fluid injection channel 33 is connected to the tube 14 in the first embodiment, and a proximal end of the tube 14 is connected to a syringe (not shown). Therefore, a fluid pushed out of the syringe by the injection unit passes through the fluid injection channel 33 and the tube 31 to flow through the injection tube 12 and is injected into an injection site such as the organ or tissue through the water-absorbing cover member 18.

Further, the proximal end of the aspiration tube 20 is fixed to a connector 35. The tube 21 is connected to a connection portion 35c formed on a side of a main body 35a of the connector 35, and the tube 21 is connected to an aspirator (not shown) and a pressure meter (not shown) such as a cavity pressure meter. Therefore, the aspiration tube 20 is configured to aspirate a fluid flowing from the water-absorbing cover member 18 into the aspiration tube 20 when the insides of the aspiration tube 20 and the tube 21 are brought into a negative pressure by the aspirator 3 (FIG. 1 and FIG. 2) in a state in which the aspiration tube 20 is fixed on an outer side of the injection tube 12 as illustrated in FIG. 16B.

A proximal end of the tube 32 is connected to an airflow channel 34, and the tube 32 and the channel 34 serve as a mechanism for enhancing the aspiration by the aspirator 3. That is, when the aspirator 3 is operated, air is sucked into the aspirator 3 through the tube 21 to bring the inside of the aspiration tube 20 into a negative pressure. In this case, the tube 32 and the channel 34 communicate to the injection tube 12, and hence air is taken into the distal end of the injection tube 12. Next, the air taken into the injection tube 12 flows between the aspiration tube 20 and the injection tube 12 at the distal end 12b of the injection tube 12 to reach the tube 21 through the connector 35. Therefore, the aspiration by the aspirator 3 is enhanced, and through the aspiration-enhanced procedure, a fluid or a body fluid can be removed more rapidly and efficiently from a fluid injection site.

During the operation of the in-situ permeation system, a fluid containing a drug and a body fluid are aspirated by the aspirator 3 through the aspiration tube 20, and thus the increase in size of a tumor as a result of the diffusion of the fluid can be avoided by the aspiration-enhanced procedure, and increase in size of the tumor can be suppressed during an in-situ permeation operation.

Figure 16D:
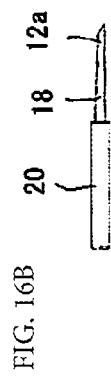

Optionally, an introduction-assisting tube 36 fixed so as to be movable on the injection tube 12 and made of a relatively hard material is used for advancing the injection tube 12 made of a soft material and the distal end 12b thereof through the connector 35. The introduction-assisting tube 36 may be made of the same material as that of the aspiration tube 20 or a material different from that of the aspiration tube 20. Prior to advancing the distal end 12b of the injection tube 12 through the connector 35 from a proximal end side of the connector 35 to a distal end side thereof under the state of FIG. 16A, the introduction-assisting tube 36 is moved along the injection tube 12 to be arranged at a position of a slit 35e, through which the injection tube 12 passes, in the proximal end of the connector 35 as illustrated in FIG. 16D. The slit 35e is formed in a film 35d made of a material such as soft plastic, for covering an opening of the proximal end of the connector 35. Next, the distal end 12b and the injection tube 12 are moved in the introduction-assisting tube 36 so as to assist the advancement of the distal end 12b and the injection tube 12 through the connector 35. In this embodiment, the slit 35e formed in the proximal end of the connector 35 serves as a fitting portion for internally fitting the injection tube 12 in the aspiration tube main body 20a.

As described above, also in the third embodiment, an intended solute and solvent are allowed to permeate and diffuse to a target tissue from the first and second injection units 6 and 9 through the injection tube 12 and the water-absorbing cover member 18. In addition, by aspirating and removing an unnecessary fluid from the connection portion 35c of the connector 35 that is connected to the aspiration tube 20 to be connected to the aspirator 3, an excessive increase in pressure in a local site is suppressed, and the diffusion of an injected fluid to the surrounding area is accelerated. Further, by providing the tube 32 and the channel 34 serving as a mechanism for enhancing aspiration, a fluid or a body fluid can be removed more rapidly and efficiently from a fluid injection site.

The present invention is described by exemplifying the first to third embodiments. However, the present invention is not limited thereto and can be variously modified as below.

Figure 17B:
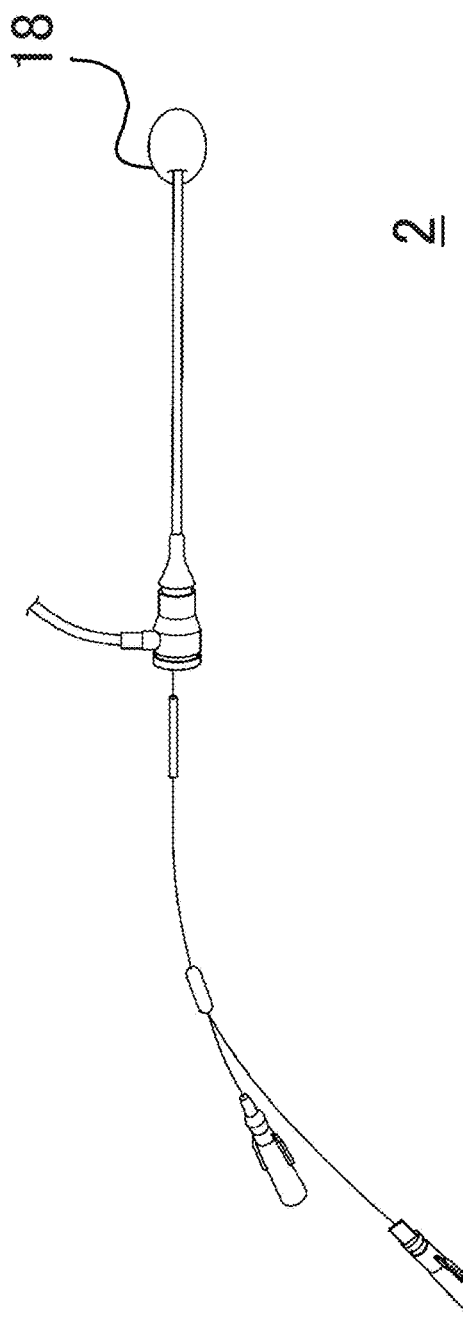
FIG. 17B is still another example of the distal end of the permeation apparatus.

The water-absorbing cover member 18 is not limited to the water-absorbing cover member 18 illustrated in FIG. 4 in the first embodiment, the water-absorbing cover member 18 illustrated in FIG. 11A and FIG. 11B in the second embodiment, and the water-absorbing cover member 18 illustrated in FIG. 16B in the third embodiment, and may be a substantially spherical water-absorbing cover member 18 as illustrated in FIG. 17A. The substantially spherical water-absorbing cover member 18 covers the distal ends of the aspiration tube 20 and the injection tube 12 and serve to diffuse a fluid such as a drug and aspirate a body fluid in the vicinity of an injection site. FIG. 17B is a photograph for showing an example of an actual permeation apparatus 2, and the water-absorbing cover member 18 is formed of a swab.

The water-absorbing cover member 18 may be omitted.

The in-situ permeation system including the permeation apparatus of any of the first to third embodiments may further include a pressure application device for bringing the pressure in a fluid injection site into a positive pressure in the same way as in the third embodiment. Specifically, referring to FIG. 19, a needle is punctured into an injection target 40 placed on the tissue table 11. The permeation apparatus 2 is connected to the injection unit 6 (and the syringe 4) through the tube 14. The permeation apparatus 2 is connected to the aspirator 3 through the tube 21, a three-way cock 45 serving as a valve mechanism, and the tube 42. The permeation apparatus 2 is connected to the pressure measurement device 41 serving as an optional pressure meter through the tube 21, a three-way cock 46 serving as a valve mechanism, and the tube 17. The permeation apparatus 2 is connected to the syringe 44 serving as the pressure application device for increasing the pressure in the injection site through a three-way cock 47 serving as a valve mechanism and a tube 43. It can be selected whether or not the permeation apparatus 2 is connected to the aspirator 3 by opening or closing the three-way cock 45. The pressure in the fluid injection site can be measured with the pressure measurement device 41 by leaving the three-way cock 46 open. When the three-way cock 47 is opened, air can be introduced into the permeation apparatus 2 from the syringe 44.

Figure 19:
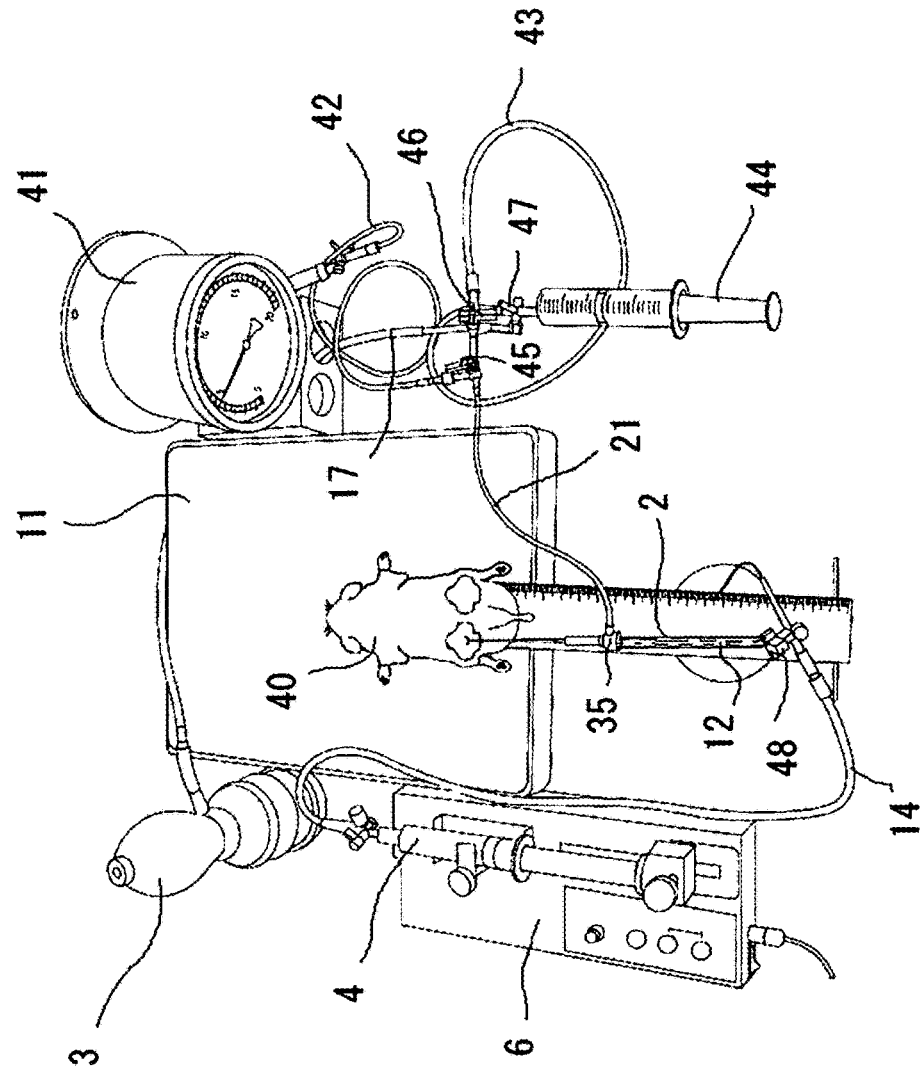
FIG. 19 is a schematic view of an in-situ permeation system based on another example of the permeation apparatus.

Specifically, when a plunger of the syringe 44 is caused to advance, air supplied from the syringe 44 is fed toward the permeation apparatus 2 through the tubes 43 and 21 serving as air supply tubes to bring the pressure in the fluid injection site into a positive pressure. More specifically, when a fluid fed from the injection unit 6 (and the syringe 4) to the permeation apparatus 2 is fed to the injection target 40 through the injection tube 12, the fluid advances also into the tube 21 at a position of the connector 35. When the plunger of the syringe 44 is caused to advance in this state, a fluid surface of the tube 21 can be moved toward the permeation apparatus 2 to such a degree as not to reach the position of the connector 35. When the three-way cock 47 is closed, the fluid injection site can be maintained under a positive pressure while being immersed with the fluid. In FIG. 19, the pressure measurement device is maintained at 5 kPa.

With the above-mentioned configuration, the pressure in the fluid injection site can be brought into a positive pressure selectively through use of the syringe 44 as well as a zero pressure or a negative pressure selectively through use of the aspirator 3. Therefore, the diffusion of a drug can be accelerated.

In the another example illustrated in FIG. 19 described above, in order to perform aspiration in an enhanced aspiration phase more rapidly and effectively, the syringe or another air supply member serving as the pressure application device may be connected to the channel 34 of FIG. 16A.

As the mechanism for enhancing aspiration, a three-way cock 48 serving as a control valve is arranged in the proximal end of the injection tube 12 as illustrated in FIG. 19 instead of arranging the two tubes 31 and 32 and the two channels 33 and 34 in the proximal end of the injection tube 12 as illustrated in FIG. 16A. Thus, air is taken into the injection tube 12 by opening the three-way cock 48 or the intake of air into the injection tube 12 is stopped by closing the three-way cock 48.

EXAMPLES

Now, the present invention is described in more detail by way of Examples.

Example 1

Figure 8B:
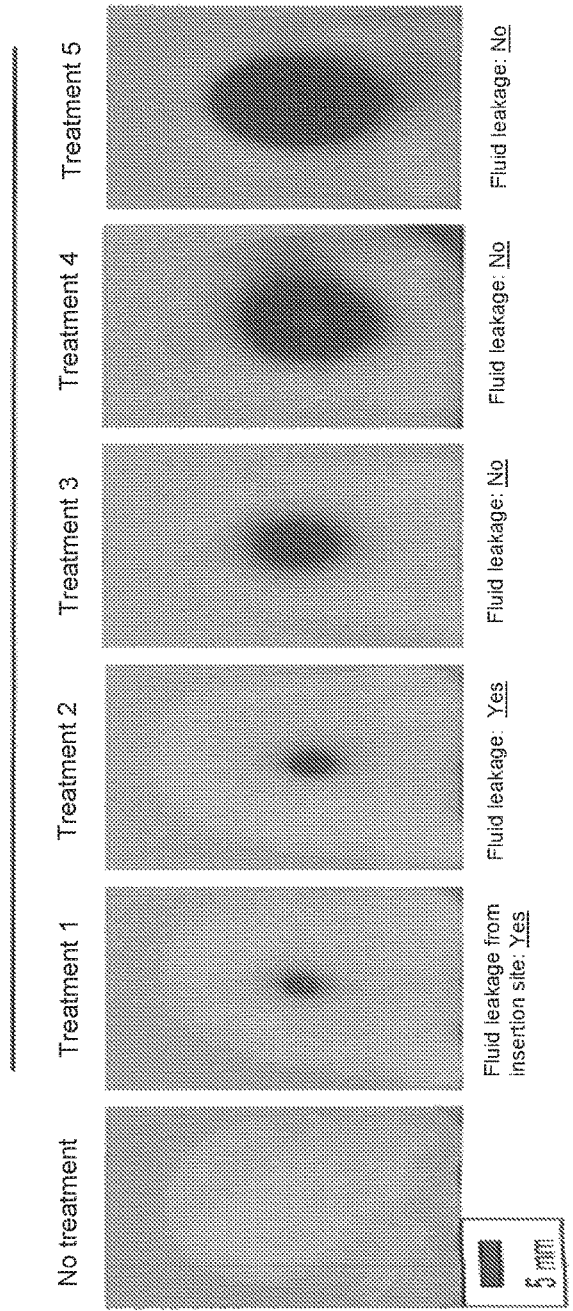

Commercially available "round Japanese radish" was hollowed out (length: 2.0 cm, width: 2.3 cm, thickness: 2.5 cm) with a metallic die and placed on a tissue table as a permeation target. A distal end of a permeation apparatus was inserted by 1.5 cm into a target tissue as illustrated in FIG. 8A (treatments 1 to 5). White arrows indicate a level of 0 cm of a cavity pressure meter. A fluid obtained by dissolving 20 mg of methylene blue as a solute (Wako Pure Chemical Industries, Ltd.) in 15 mL of absolute ethanol as a solvent (manufactured by Mylan Inc.) was caused to permeate the round Japanese radish hollowed out as in the treatments 1 to 5. The results are shown in FIG. 8B.

Non-Treatment: Control

Treatment 1: A 22-gauge (length: 7 cm) syringe needle was inserted by 1.5 cm into a target tissue, and 100 µL of a fluid was injected into the target tissue at once in 1 second. The resultant target tissue was left to stand still for 120 minutes.

Treatment 2: A syringe needle was inserted by 1.5 cm into a target tissue similarly to the treatment 1, and 100 µl of a fluid was injected into the target tissue over 2 hours through use of a microsyringe pump. First, the fluid was injected at a rate of 0.5 µL per minute over 40 minutes, and thereafter injected at a rate of 1 µL per minute over 80 minutes.

Treatment 3: 100 µL of a fluid was injected into a target tissue at once in 1 second through use of the permeation apparatus of FIG. 3, and the resultant target tissue was left to stand still for 120 minutes.

Treatment 4: First, 100 µL of a fluid was injected into a target tissue at once through use of the permeation apparatus of FIG. 3 similarly to the treatment 3. Then, the injection (5 minutes) and the aspiration (1 minute) of the fluid were repeated through use of a microsyringe pump at a rate of perfusing 100 µL of the fluid in 6 minutes, and the fluid was perfused for a total of 120 minutes. At any point of time, the fluid surface was adjusted by aspiration so as not to exceed the "0" cm level of the cavity pressure meter, and the fluid was controlled so as not to leak from the insertion site.

Treatment 5: The fluid was perfused for a total of 120 minutes through use of the permeation apparatus of FIG. 3 similarly to the treatment 4. In this case, the injection amount, the injection rate, and the aspiration timing were adjusted so that the fluid surface exceeded the "15 cm" level of the cavity pressure meter for the longest possible time period and the fluid did not leak from the insertion site.

In the targets subjected to the permeation in the treatments 1 to 5, each target was cut at a position of 2 mm, 4 mm, and 6 mm of the insertion site in a range of from the distal end of the insertion site to a position of 8 mm back from the distal end. After that, those cut targets were photographed, and typical photographs are shown in FIG. 8B.

Further, regarding the treatment 1 (group 1) to the treatment 5 (group 5), an experiment was conducted with respect to three different targets (n=3). A vertical axis and a horizontal axis of a circular (elliptical) portion stained with methylene blue as shown in the photographs of FIG. 8B were measured with a ruler with respect to each "target", and each length was divided by 2 to obtain numerical values "a" and "b". The area of the elliptical portion stained with methylene blue was calculated by (3.14×a×b). The values of the calculated areas of the five treatment groups are shown in a graph of FIG. 9 as areas that methylene blue has permeated. Statistical analysis was performed between the respective groups regarding the "permeated area" through use of a Fisher's PLSD method. The significance level was set to 5%.

Figure 9:
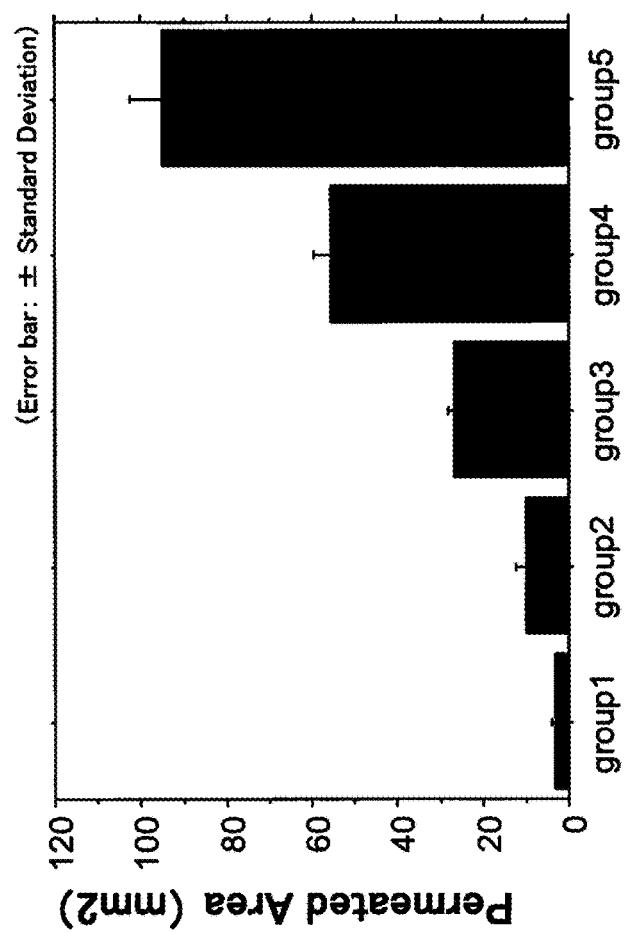
FIG. 9 is a graph for showing the area of diffusion of the injected fluid.

The treatment 2 of FIG. 9 was performed as a CED method that was a typical related-art method. It was clarified that the permeation and diffusion method of the treatments 4 and 5 of the present invention was more excellent than the related-art CED method. Further, in the group 5 of the treatment 5 controlled in a state in which an in-situ cavity internal pressure was increased more, the permeation and diffusion were enabled in a wider area compared to the group 4 of the treatment 4 under a lower in-situ cavity internal pressure. The area of permeation and diffusion can be controlled with an in-situ cavity internal pressure, and hence an optimum in-situ cavity internal pressure can be selected depending on each case.

According to the present invention, compared to the related-art method, the permeation and diffusion of a solute and/or a solvent were enabled more efficiently (in a wider area) and more uniformly (in a concentric shape).

Example 2

A Syrian hamster (6-week-old male) was subcutaneously transplanted with 16,500,000 RPMI 1846 skin cancer cells derived from the same species to obtain a subcutaneously-transplanted hamster model as described below. The distal end of the permeation apparatus 2 was inserted into a tumor tissue (target) as shown in FIG. 10B. An experiment was conducted through use of a fluid obtained by dissolving 20 mg of methylene blue (Wako Pure Chemical Industries, Ltd.) as a solute in 15 mL of absolute ethanol (manufactured by Mylan Inc.) as a solvent and the permeation apparatus of FIG. 3B. First, 100 µL of the fluid was injected into the target at once, and thereafter the fluid was injected manually at a rate of perfusing 50 µL of the fluid in 1 minute. The fluid was perfused for a total of 30 minutes. The fluid surface was adjusted so as not to exceed the "0" cm level of the cavity pressure meter at any time point by appropriately performing aspiration. The results are shown in FIG. 10C.

As shown in FIG. 10C, the permeation apparatus of the present invention is applicable to a therapeutic method and an examination method requiring the uniform permeation and diffusion of a solute and/or a solvent in a tumor.

Example 3

A Syrian hamster (13-week-old male) was subcutaneously transplanted with RPMI 1846 skin cancer cells derived from the same species to obtain a subcutaneously-transplanted hamster model as described below. The distal end of the permeation apparatus 2 was inserted into a tumor tissue (target) as shown in FIG. 13A. An experiment was conducted through actual use of a fluid obtained by dissolving 30 mg of methylene blue ("Methylene Blue", manufactured by Wako Pure Chemical Industries, Ltd.) as a solute in 15 mL of 50% acetic acid (prepared by diluting, with pure water, "017-00256", manufactured by Wako Pure Chemical Industries, Ltd.) as a solvent and the permeation apparatus of FIG. 12 and FIG. 13B. The fluid was injected into the target with the syringe 4 ("1005TLL 5 ML SYR", manufactured by Hamilton Company) through use of the injection unit 6 ("Microsyringe Pump MSPE-3, manufactured by AS ONE Corporation) at a rate of perfusing from 50 µL to 100 µL of the fluid in 1 minute. The fluid was perfused for a total of 60 minutes. The fluid was adjusted so as not to leak to an outside from the insertion site of the permeation apparatus 2 at any time point by appropriately performing aspiration with the aspirator 3 ("MMI Manual Aspirator", manufactured by Muranaka Medical Instruments Co., Ltd.).

Figure 13B:
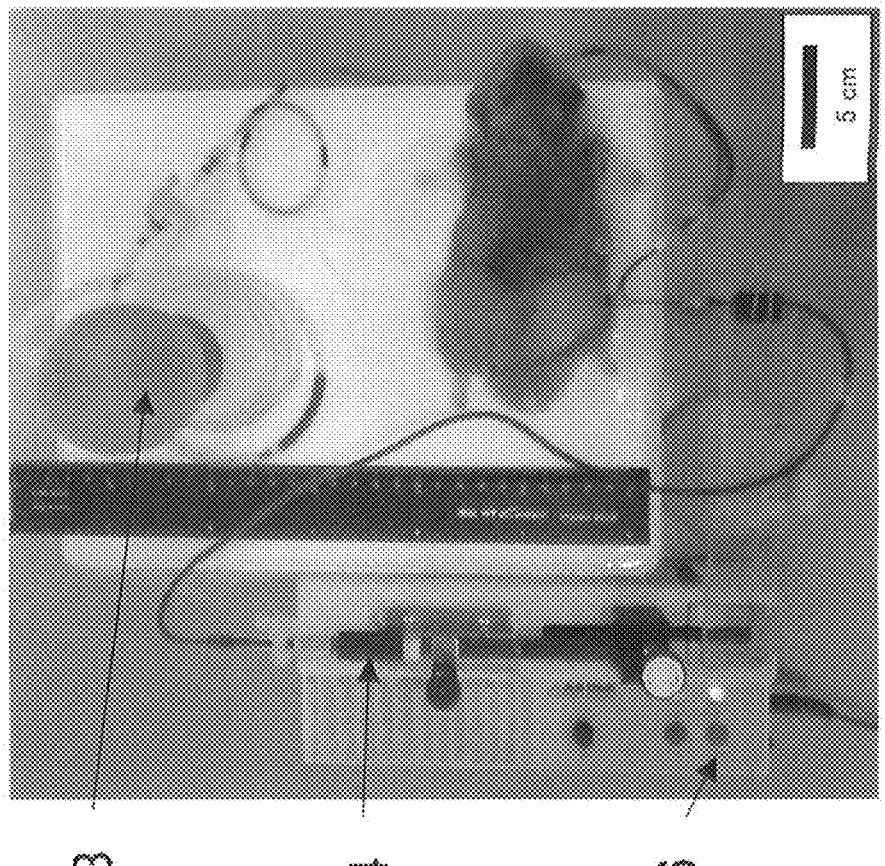
FIG. 13B is a photograph of an experimental result for showing the injection apparatus of the present invention and the usefulness thereof.
Figure 13A:
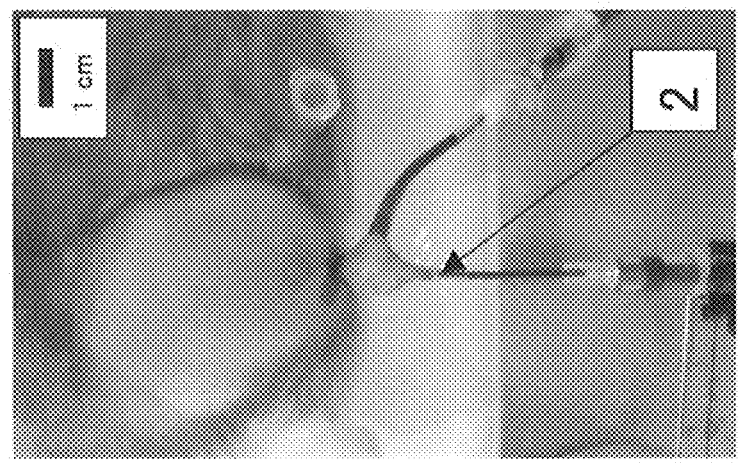
FIG. 13A is a photograph for showing a state in which a fluid is being injected into a tumor through use of the permeation apparatus.

A photograph (permeation apparatus and tumor) during actual injection (perfusion) is shown in FIG. 13A, and a photograph (entire image) during actual injection (perfusion) is shown in FIG. 13B. Further, the results after the injection of methylene blue are shown in FIG. 14A and illustrated in FIG. 14B. In the tumor in this experiment, a large number of capsules and other septums existed macroscopically (FIG. 14A). That is, a main body of the tumor was formed of a plurality of tumors encapsulated with different capsules. The permeation apparatus was (consequently) inserted into the largest tumor positioned at the center portion of the main body of the tumor. Further, through the appropriate aspiration, the fluid was able to be adjusted so as not to leak to an outside from the insertion site of the permeation apparatus at any time point (FIG. 14B). As a result, it was verified that the method and the apparatus of the present invention were applicable to a wide range of therapeutic and examination methods requiring the uniform permeation and diffusion of a solute and/or a solvent (beyond the septums in the tumor) in the tumor.

Example 4

Figure 15A:
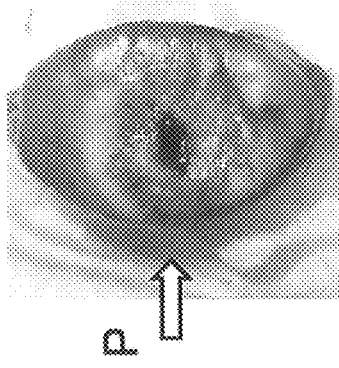
FIG. 15A is a photograph for showing a state of diffusion of methylene blue in a tumor after the injection of the methylene blue in Example 4.
Figure 15B:
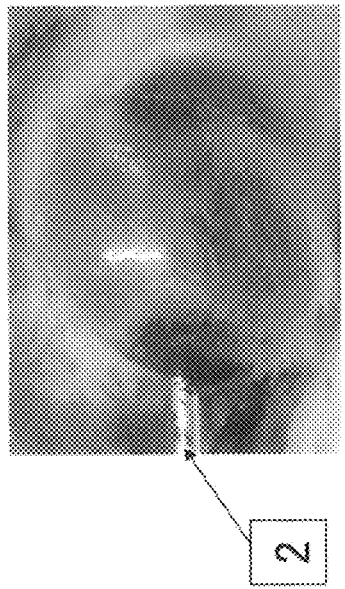
FIG. 15B is a photograph for showing tumor sections (the tumor was divided into two parts with reference to the division line L of FIG. 15C) after the injection of the methylene blue. The arrow denoted by P indicates an insertion direction of the permeation apparatus.
Figure 15C:
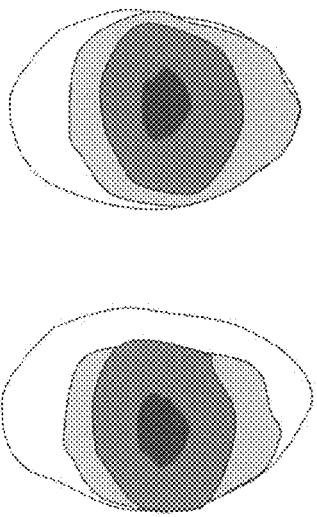
FIG. 15C is an image for illustrating the tumor of FIG. 15 Although color coding.
Figure 15D:
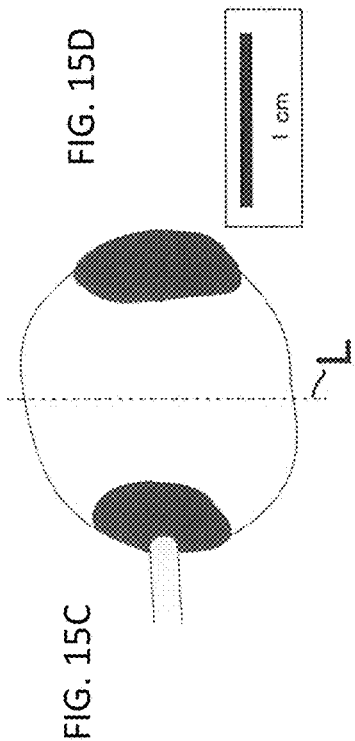

A Syrian hamster (13-week-old male) was subcutaneously transplanted with RPMI 1846 skin cancer cells derived from the same species to obtain a subcutaneously-transplanted hamster model as described below. The distal end of the permeation apparatus was inserted into a tumor tissue (target) as shown in FIG. 15A. An experiment was conducted through use of a fluid obtained by dissolving 30 mg of methylene blue ("Methylene Blue", manufactured by Wako Pure Chemical Industries, Ltd.) as a solute in 15 mL of 50% acetic acid (prepared by diluting, with pure water, "017-00256", manufactured by Wako Pure Chemical Industries, Ltd.) as a solvent and a permeation apparatus similar to the permeation apparatus of FIG. 12. The fluid was injected with the injection unit at a rate of perfusing from 50 µL of the fluid in 1 minute. Aspiration was performed appropriately, and the fluid was perfused for a total of 90 minutes. The results are shown in FIG. 15A to FIG. 15D. The tumor in this experiment was formed of a single tumor containing no capsules and other septums macroscopically (FIG. 15A and FIG. 15B). The permeation apparatus was inserted into a center portion of a main body of the tumor. As a result, it was verified that the method and the apparatus of the present invention were applicable to a wide range of therapeutic and examination methods requiring the (concentric) uniform permeation and diffusion of a solute and/or a solvent in the tumor.

Example 5

A Syrian hamster (8-week-old male) was subcutaneously transplanted with RPMI 1846 skin cancer cells derived from the same species to obtain a subcutaneously-transplanted hamster model. The distal end of the permeation apparatus 2 was inserted into a tumor tissue (target). An experiment was conducted through use of a fluid obtained by dissolving 30 mg of methylene blue ("Methylene Blue", manufactured by Wako Pure Chemical Industries, Ltd.) as a solute in 15 mL of 50% acetic acid (prepared by diluting, with pure water, "017-00256", manufactured by Wako Pure Chemical Industries, Ltd.) as a solvent and a permeation apparatus similar to the permeation apparatus of FIG. 16. The fluid was injected into the target through use of the injection unit by perfusing the fluid at a rate of 100 µL/min for 45 minutes and then 250 µL/min for 15 minutes (total: 60 minutes). After the injection was stopped, an air flow was introduced through the air supply tubes of the permeation apparatus 2, and aspiration was performed appropriately in an enhanced aspiration phase. As a result, as shown in FIG. 18A to FIG. 18C, it was verified that the size of the tumor was maintained during an in-situ permeation (ISP) operation, and the increase in size of the tumor as a result of the diffusion of the fluid containing a drug was able to be avoided.

The present invention can be used in a situation requiring that a solute, a solvent, a drug, cells, or the like is caused to permeate and diffuse to a local site of a living body in the medical field (including therapy of cancer, regeneration medicine, and drug delivery such as delivery of a drug to a local site). More specifically, the present invention can be used for causing a drug such as an anticancer drug, ethanol, or acetic acid to permeate and diffuse to a cancer lesion, resulting in tumor regression, or for causing a drug, cells, or the like, which is required in the process of production of an organ, a tissue, or the like to be used for regeneration medicine, to permeate and diffuse into the target tissue. Further, Examples of the present application exemplify the diffusion and permeation of a fluid to a target tissue in an in-situ cavity in a shape exhibited by the form of PVA of FIG. 3A and FIG. 3B. However, the form of the PVA can be changed freely in accordance with the shape of an actual in-situ cavity and/or the size thereof. That is, by using the method of the present invention, an intended fluid is allowed to permeate and diffuse to a target tissue in in-situ cavities having various forms and/or sizes.

Besides the use for in-situ administration of a drug or the like in a living body in the medicine and the like described above, the present invention can be used in a substance, a natural object, and a product (including a food product, an industrial product, etc.) in which the control of the permeation and diffusion of a solute and/or a solvent is useful. Further, the present invention can be used in a water-containing (wet) substance, a dry substance, and the like. Further, any substance can be a target as long as the permeation and diffusion of the substance can be performed, irrespective of whether the substance is derived from a living body or a nonliving body.

What is claimed is:
1. A permeation apparatus connected to an aspirator and an injection apparatus, for injecting and aspirating a fluid to and from a target injection site, the permeation apparatus, comprising:
an aspiration tube connectable to the aspirator;
an injection tube connectable to the injection apparatus, the injection tube having a distal end, the injection tube being insertable in the aspiration tube; and
a water-absorbing cover member covering the distal end of the injection tube in contact with the distal end of the injection tube, the water-absorbing cover member having a distal end, wherein the distal end of the water-absorbing cover member is located outside the aspiration tube, and wherein the injection tube and the water-absorbing cover member are movable relative to the aspiration tube, and the aspiration tube being configured to aspirate a fluid flowing from the water-absorbing cover member into the aspiration tube.

2. The permeation apparatus according to claim 1, further comprising a cavity pressure tube.

3. The permeation apparatus according to claim 2, wherein a distal end of the aspiration tube, the distal end of the injection tube, and a distal end of the cavity pressure tube are covered with the water-absorbing cover member.

4. The permeation apparatus according to claim 1, wherein at least one of the aspiration tube or the injection tube has at least one hole on a side surface thereof.

5. The permeation apparatus according to claim 1,
wherein the aspiration tube comprises an aspiration tube main body and a connection portion to be connected to the aspirator,
wherein the injection tube is internally fitted in the aspiration tube main body, and the distal end of the injection tube is covered with the water-absorbing cover member, and
wherein the water-absorbing cover member on a side of a syringe is arranged in the aspiration tube so that the aspirator is capable of aspirating the fluid flowing from the water-absorbing cover member into the aspiration tube.

6. The permeation apparatus according to claim 1, wherein the permeation apparatus is used in combination with a puncture needle and a hollow tube capable of covering the puncture needle and allowing the permeation apparatus to be inserted in the hollow tube.

7. The permeation apparatus of claim 1, wherein the permeation apparatus is assembled by puncturing an injection site with a puncture needle through an aspiration tube main body, pulling out the puncture needle, then inserting the injection tube into a puncture site through the aspiration tube main body, and fitting the injection tube in the aspiration tube main body.

8. The permeation apparatus according to claim 1, wherein the water-absorbing cover member is wrapped around an outer peripheral surface of the distal end of the injection tube, and a fluid injected into the injection tube is diffused through the water-absorbing cover member.

9. The permeation apparatus according to claim 1, wherein the water-absorbing cover member is made of a material capable of absorbing and retaining a fluid.

10. The permeation apparatus according to claim 1, wherein the water-absorbing cover member is made of a material capable of absorbing and retaining a fluid selected from a hydrophilic polymer, a foam, a knitted and woven fabric and a nonwoven fabric.

11. The permeation apparatus according to claim 1, wherein the permeation apparatus is a permeation apparatus for treating a tumor and a fluid injected to the target injection site includes acetic acid.

12. A permeation apparatus connected to an aspirator and an injection apparatus, for injecting and aspirating a fluid to and from a target injection site, the permeation apparatus comprising:
an aspiration tube connectable to the aspirator;
an injection tube connectable to the injection apparatus, the injection tube having a distal end, the injection tube being insertable in the aspiration tube;
a water-absorbing cover member covering the distal end of the injection tube, the water-absorbing cover member having a distal end, the distal end of the water-absorbing cover member located outside of the aspiration tube,
a tube communicating to the injection tube, for supplying air,
the injection tube and the water-absorbing cover member being movable relative to the aspiration tube,
the aspirator being configured to aspirate a fluid flowing into the aspiration tube through the aspiration tube, and
a tube connecting the aspiration tube to the aspirator,
the air being taken into the tube connecting the aspiration tube to the aspirator through the tube for supplying the air at a time of the aspiration.

13. The permeation apparatus of claim 12, wherein the permeation apparatus is assembled by puncturing an injection site with a puncture needle through an aspiration tube main body, pulling out the puncture needle, then inserting the injection tube into a puncture site through the aspiration tube main body, and fitting the injection tube in the aspiration tube main body.

14. The permeation apparatus according to claim 12, wherein the water-absorbing cover member is made of a material capable of absorbing and retaining a fluid.

\* \* \* \* \*